(12) United States Patent
Aoki

(10) Patent No.: US 8,291,893 B2
(45) Date of Patent: Oct. 23, 2012

(54) DEVICE FOR DETERMINING ACTIVATION OF EXHAUST GAS SENSOR AND CONTROL DEVICE FOR INTERNAL COMBUSTION ENGINE

(75) Inventor: Keiichiro Aoki, Sunto-gun (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 82 days.

(21) Appl. No.: 13/061,850

(22) PCT Filed: Oct. 1, 2009

(86) PCT No.: PCT/JP2009/067148
§ 371 (c)(1),
(2), (4) Date: Mar. 2, 2011

(87) PCT Pub. No.: WO2010/041585
PCT Pub. Date: Apr. 15, 2010

(65) Prior Publication Data
US 2011/0155113 A1 Jun. 30, 2011

(30) Foreign Application Priority Data
Oct. 9, 2008 (JP) ................................. 2008-263139

(51) Int. Cl.
*F02D 41/04* (2006.01)
*F02D 41/00* (2006.01)
(52) U.S. Cl. ........................................ 123/672; 123/676
(58) Field of Classification Search .................. 123/672, 123/676, 688, 689, 690, 697, 703; 701/109
See application file for complete search history.

(56) References Cited

U.S. PATENT DOCUMENTS

| 5,036,820 A * | 8/1991 | Fujimoto et al. ............... 123/686 |
| 5,462,040 A * | 10/1995 | Krebs et al. .................... 123/688 |
| 6,332,966 B1 | 12/2001 | Sakai et al. |
| 2003/0019486 A1 * | 1/2003 | Hada et al. ..................... 123/697 |

(Continued)

FOREIGN PATENT DOCUMENTS
JP 61-241652 A 10/1986
(Continued)

OTHER PUBLICATIONS

International Preliminary Report on Patentability issued in PCT/JP2009/067148 dated May 19, 2011 (5 pages).

*Primary Examiner* — Mahmoud Gimie
(74) *Attorney, Agent, or Firm* — Sughrue Mion, PLLC

(57) ABSTRACT

The invention has an object to provide a device for determining activation of an exhaust gas sensor which accurately determines a time at which an exhaust gas sensor output is usable, and can suppress an adverse effect caused by use of the exhaust gas sensor output including a large effect of adsorbed species. A time is measured from a time point when a temperature of an air-fuel ratio sensor 48 reaches a predetermined temperature T1, while the air-fuel ratio sensor 48 is warmed up. When the time becomes a predetermined target holding time Te or more, the air-fuel ratio sensor 48 is determined as being in an activation state. The target holding time Te is preferably set at such a length that all adsorbed species adsorbed onto the air-fuel ratio sensor 48 are desorbed, and areas around a sensor element section 50 are completely replaced with an exhaust gas.

17 Claims, 12 Drawing Sheets

U.S. PATENT DOCUMENTS

| | | |
|---|---|---|
| 2004/0074773 A1 | 4/2004 | Niwa |
| 2005/0029098 A1 | 2/2005 | Aoki et al. |
| 2007/0204840 A1 * | 9/2007 | Abe .............................. 123/697 |

FOREIGN PATENT DOCUMENTS

| | | |
|---|---|---|
| JP | 08-075695 A | 3/1996 |
| JP | 2000-180400 A | 6/2000 |
| JP | 2001-013107 A | 1/2001 |
| JP | 2004-132840 A | 4/2004 |
| JP | 2004-211611 A | 7/2004 |
| JP | 2005-055279 A | 3/2005 |
| JP | 2005-207924 A | 8/2005 |
| JP | 2006-170849 A | 6/2006 |
| JP | 2008-138569 A | 6/2008 |

* cited by examiner

Fig.9

| THWI (water temperature °C) | -10 | 0 | 10 | 40 |
|---|---|---|---|---|
| TWACT (time sec) | 5 | 3 | 2 | 0 |

*Fig.11*

| TIMPI (impedance value Ω) | 100°C corresponding value | 250°C corresponding value | 300°C corresponding value | 700°C corresponding value |
|---|---|---|---|---|
| TIACT (time sec) | 5 | 1 | 0 | 0 |

*Fig.13*

| AFBACTP<br>(rich side A/F peak value A/F) | 11 | 12 | 14 | 14.6 |
|---|---|---|---|---|
| TAFPACT<br>(time sec) | 5 | 3 | 1 | 0 |

# DEVICE FOR DETERMINING ACTIVATION OF EXHAUST GAS SENSOR AND CONTROL DEVICE FOR INTERNAL COMBUSTION ENGINE

This application is a National Stage of International Application No. PCT/JP2009/067148 filed Oct. 1, 2009, claiming priority based on Japan Patent Application No. 2008-263139 filed Oct. 9, 2008, the contents of all of which are incorporated herein by reference in their entirety.

TECHNICAL FIELD

The invention relates to a device for determining activation of an exhaust gas sensor, and a control device for an internal combustion engine.

BACKGROUND ART

As shown in, for example, Japanese Patent Laid-Open No. 2008-138569, a technique of controlling an air-fuel ratio of an internal combustion engine using the output of an exhaust gas sensor has been conventionally used. An exhaust gas sensor issues an output corresponding to the air-fuel ratio of an exhaust gas by reaching an activation temperature. There is a demand for early start of air-fuel ratio control using an exhaust gas sensor output in order to obtain a favorable emission characteristic early at the time of start of an internal combustion engine. In order to satisfy the demand, a heater is usually provided inside an exhaust gas sensor, and the heater quickly heats the exhaust gas sensor to a predetermined activation temperature at the time of start of an internal combustion engine.

Incidentally, there is the case in which the output from an exhaust gas sensor can be used without any problem if only specific conditions are satisfied, even before the exhaust gas sensor reaches the activation temperature, that is, even before the regular activation state. Thus, even before the regular activation state, by determining the state in which the output of the exhaust gas sensor is usable, that is, a semi-activation state, the output of the exhaust gas sensor can be used for air-fuel ratio control at an earlier stage.

However, while an internal combustion engine stops, exhaust gas components adsorb on the electrode portions of the exhaust gas sensor, the porous body portion of the sensor element and the like. Hereinafter, the exhaust gas components which adsorb on the exhaust gas sensor will also be generically described as "adsorbed species". While the exhaust gas sensor is heated at the time of start of an internal combustion engine, the adsorbed species start to be desorbed. The adsorbed species which are desorbed are present in the vicinity of the exhaust gas sensor, and thereby, influences the output of the exhaust gas sensor, and inhibit accurate measurement of the exhaust gas air-fuel ratio. While the effect of the adsorbed species remains, the exhaust gas sensor output does not indicate the accurate value of the air-fuel ratio of the exhaust gas. As above, there is the problem that an output shift occurs due to the effect of the adsorbed species which are desorbed, and early use of the exhaust sensor output is inhibited.

Thus, in the air-fuel ratio control device according to Japanese Patent Laid-Open No. 2008-138569, the output value of the exhaust gas sensor is masked during the time period until the exhaust gas sensor reaches a regular activation state after a semi-activation state under the situation in which the effect of the adsorbed species is worried about. Thereby, the measures for preventing the adverse effect of the output shift due to adsorbed species can be taken in accordance with necessity.

CITATION LIST

Patent Literature

Patent Literature 1: Japanese Patent Laid-Open No. 2008-138569
Patent Literature 2: Japanese Patent Laid-Open No. 2005-207924
Patent Literature 3: Japanese Patent Laid-Open No. 8-75695
Patent Literature 4: Japanese Patent Laid-Open no. 2006-170849
Patent Literature 5: Japanese Patent Laid-Open No. 2004-211611

SUMMARY OF INVENTION

Technical Problem

As described above, there is generally the demand for early start of the air-fuel ratio control using the output of an exhaust gas sensor at the time of actuation of an internal combustion engine. In order to meet the demand, the above described prior art basically uses the exhaust gas sensor output in a semi-activation state, and as an exception, it masks the exhaust gas sensor output during the time period until a regular activation state from a semi-activation state under the situation where the effect of adsorbed species is worried about.

As described above, the adsorbed species are desorbed from the exhaust gas sensor while the exhaust gas sensor is being heated at the time of start of an internal combustion engine. Here, the inventor of the present application has found out that the effect of the adsorbed species can still remain after the exhaust gas sensor reaches the activation temperature, that is, the effect of the adsorbed species can still remain even when the exhaust gas sensor has a sufficiently high temperature.

The art of the above described Patent Literature 1 masks the exhaust gas sensor output during the time period until the regular activation from semi-activation, but starts air-fuel ratio control (feedback control) using the exhaust gas sensor output after the regular activation. Therefore, in the above described prior art, the air-fuel ratio control using the output of the exhaust gas sensor is started, though a large effect of the adsorbed species is included in the output of the exhaust gas sensor when the large effect of the adsorbed species still remains after regular activation. Like this, the prior arts still have a room for improvement in the respect of avoidance of the adverse effect caused by adsorbed species.

The present invention is made for solving the problem as described above, and has an object to provide a device for determining activation of an exhaust gas sensor, which accurately determines the time when an exhaust gas sensor output is usable, and can suppress an adverse effect due to use of the exhaust gas sensor output including a large effect of adsorbed species.

Further, the present invention has an object to provide a control device for an internal combustion engine including a configuration which suppresses a harmful effect of a shift of a sensor output due to adsorbed species at a time of start of the engine.

Solution to Problem

To achieve the above-mentioned purpose, a first aspect of the present invention is a device for determining activation of an exhaust gas sensor, comprising:

a heater for heating the exhaust gas sensor at a time of start of an internal combustion engine; and determining means which determines an activation state of the exhaust gas sensor based on whether or not such a time period that desorbed species are substantially eliminated from the exhaust gas sensor has elapsed after the adsorbed species which are exhaust gas components adsorbed on the exhaust gas sensor start to be desorbed, at the time of start of the internal combustion engine.

A second aspect of the present invention is the device for determining activation of an exhaust gas sensor according to the first aspect, further comprising:

acquiring means which acquires a physical amount having a correlation with a temperature of the exhaust gas sensor, wherein the determining means includes temperature determining means which determines whether or not the temperature of the exhaust gas sensor has reached a predetermined temperature which is set in advance within a temperature region not lower than a desorption start temperature which is a temperature at which the adsorbed species which are the exhaust gas components adsorbed on the exhaust gas sensor start to be desorbed, based on the physical amount, and activation determining means which determines the activation state of the exhaust gas sensor based on an elapsed time from a time point when the temperature of the exhaust gas sensor reaches the predetermined temperature.

A third aspect of the present invention is the device for determining activation of an exhaust gas sensor according to the first aspect, further comprising:

acquiring means which acquires a physical amount having a correlation with a temperature of the exhaust gas sensor, wherein the heater heats the exhaust gas sensor to a target temperature at the time of start of the internal combustion engine, and the determining means includes activation determining means which determines the activation state of the exhaust gas sensor based on an elapsed time from a time point when the temperature of the exhaust gas sensor reaches a predetermined temperature which is set in advance in a temperature region not higher than the target temperature, after start of heating of the heater.

A fourth aspect of the present invention is the device for determining activation of an exhaust gas sensor according to the second aspect or the third aspect, wherein the activation determining means determines the activation state of the exhaust gas sensor based on the temperature of the exhaust gas sensor and the elapsed time, and the activation determining means includes activation temperature determining means which determines the activation state of the exhaust gas sensor based on whether or not the exhaust gas sensor reaches an activation temperature, and activation determination prohibiting means which prohibits the exhaust gas sensor from being determined as reaching the activation state irrespective of a determination result of the activation temperature determining means until the elapsed time exceeds a predetermined time.

A fifth aspect of the present invention is the device for determining activation of an exhaust gas sensor according to the fourth aspect, further comprising:

means which sets the predetermined time so that a time at which prohibition by the activation determination prohibiting means is released is past a time at which the exhaust gas sensor reaches the activation temperature by the heater which heats the exhaust gas sensor at the time of start of the internal combustion engine.

A sixth aspect of the present invention is the device for determining activation of an exhaust gas sensor according to the second aspect or the third aspect, wherein the predetermined temperature is an activation temperature of the exhaust gas sensor, and the activation determining means determines that the exhaust gas sensor is in the activation state when a predetermined time elapses after the exhaust gas sensor reaches the activation temperature.

A seventh aspect of the present invention is the device for determining activation of an exhaust gas sensor according to the second aspect or the third aspect, wherein the activation determining means determines the activation state of the exhaust gas sensor based on whether or not the elapsed time has exceeded a predetermined time, and the predetermined time is set so as to pass a time point at which the exhaust gas sensor reaches an activation temperature by heating of the heater, and is set at such a length that an output shift of the exhaust gas sensor due to adsorbed species is substantially eliminated.

An eighth aspect of the present invention is the device for determining activation of an exhaust gas sensor according to any one of the second to the seventh aspects, wherein the predetermined temperature is a temperature selected from a temperature region from 300° C. to 700° C. inclusive.

A ninth aspect of the present invention is the device for determining activation of an exhaust gas sensor according to any one of the second to the seventh aspects, wherein the physical amount acquired by the acquiring means is an impedance or an admittance of the exhaust gas sensor, and the predetermined temperature is a temperature selected from a temperature region not less than 400° C.

A tenth aspect of the present invention is the device for determining activation of an exhaust gas sensor according to any one of the fourth to the ninth aspects, further comprising:

property acquiring means which acquires a fuel property of an internal combustion engine; and property condition time setting means which sets the predetermined time to a different length in accordance with a fuel property acquired by the property acquiring means.

An eleventh aspect of the present invention is the device for determining activation of an exhaust gas sensor according to any one of the fourth to the tenth aspects, further comprising:

rich peak acquiring means which acquires a peak value at a rich side of an air-fuel ratio indicated by an output of the exhaust gas sensor in a time period in which the exhaust gas sensor is inactive, during start of an internal combustion engine, and rich condition time setting means which sets the predetermined time to be longer as the air-fuel ratio acquired by the rich peak acquiring means is larger to a rich side.

A twelfth aspect of the present invention is the device for determining activation of an exhaust gas sensor according to any one of the fourth to the eleventh aspects, further comprising:

adsorption amount acquiring means which acquires an amount having a correlation with an adsorption amount at a time of stop, which is an amount of gas components adsorbed onto the exhaust gas sensor while an internal combustion engine is stopped; and adsorption amount condition time setting means which changes the predetermined time in accordance with an amount which is acquired by the adsorption amount acquiring means.

A thirteenth aspect of the present invention is the device for determining activation of an exhaust gas sensor according to the twelfth aspect, wherein the adsorption amount acquiring means includes means for acquiring at least one of a water temperature, an intake air temperature and an oil temperature at the time of start of the internal combustion engine, an exhaust gas sensor temperature at the time of start of the internal combustion engine and a physical amount having a correlation with the exhaust gas sensor temperature, and a stop time period which is a length of a time period from stop of the internal combustion engine to a beginning of start of the internal combustion engine, and the adsorption amount condition time setting means includes means which sets the predetermined time to be longer as the water temperature or the oil temperature at the time of start of the internal combustion is lower, as the exhaust gas sensor temperature at the time of start of the internal combustion engine is lower, or the stop time period is longer.

A fourteenth aspect of the present invention is the device for determining activation of an exhaust gas sensor according to the fourth to the tenth aspects, further comprising:

at least one pair of the rich peak acquiring means and the rich condition time setting means according to the eleventh aspect, and the adsorption amount acquiring means and the adsorption amount condition time setting means according to the twelfth aspect of the thirteenth aspect, and instant activation determining means which determines that the exhaust gas sensor is in the activation state when the exhaust gas sensor reaches the activation temperature, when an air-fuel ratio acquired by the rich peak acquiring means indicates stoichiometry or a value at a lean side, or/and when an adsorption amount indicated by the adsorption amount acquiring means is below a predetermined reference value.

A fifteenth aspect of the present invention is the device for determining activation of an exhaust gas sensor according to the first aspect, wherein the determining means determines whether after adsorbed species which are exhaust gas components adsorbed onto the exhaust gas sensor start to be desorbed, such a time period that the adsorbed species are substantially eliminated from the exhaust gas sensor has elapsed or not, based on a result of measurement with at least one of an integrated air amount of the internal combustion engine, an element temperature of the exhaust gas sensor, and an element admittance of the exhaust gas sensor, as a target.

To achieve the above-mentioned purpose, a sixteenth aspect of the present invention is a control device for an internal combustion engine, comprising:

an exhaust gas sensor;

the device for determining activation of the exhaust gas sensor according to any one of the first to the fifteenth aspects which performs determination of activation of the exhaust gas sensor;

feedback control means for performing feedback control of an air-fuel ratio of the internal combustion engine based on an output of the exhaust gas sensor; and feedback control starting means which starts control by the feedback control means based on a result of the determination of the device for determining activation, at a time of start of the internal combustion engine.

A seventeenth aspect of the present invention is the control device for an internal combustion engine according to the sixteenth aspect, wherein the exhaust gas sensor is a critical current type air-fuel ratio sensor.

Advantageous Effects of Invention

According to the first invention, the determining means can determine that the exhaust gas sensor is in the activation state at the time point when the output shift of the exhaust gas sensor due to adsorbed species is eliminated. Thereby, use of the exhaust gas sensor output including a large effect of the adsorbed species can be suppressed.

According to the second invention, the activation state of the exhaust gas sensor can be determined with consideration given to the elapsed time from the time point at which the temperature of the exhaust gas sensor reaches the desorption start temperature. If the temperature of the exhaust gas sensor rises to a certain extent, the output characteristic of the exhaust gas sensor itself is stabilized. However, the effect of the adsorbed species sometimes remains even when the exhaust gas sensor reaches a high temperature. If the exhaust gas sensor is under the environment at a temperature of the desorption start temperature or higher, the amount of the desorbed species decreases in accordance with the lapse of time. Thus, in the second invention, the time is measured with the time point at which the exhaust gas sensor temperature reaches a predetermined temperature of the desorption start temperature or higher set as a starting point. The elapsed time after the exhaust gas sensor reaches the predetermined temperature is included in the basis of activation determination, and thereby, the elimination degree of the effect of the adsorbed species can be reflected in the activation determination. Thereby, use of the exhaust gas sensor output including a large effect of the adsorbed species can be suppressed.

According to the third invention, in the process of rise of the temperature of the exhaust gas sensor, the activation state of the exhaust gas sensor can be determined with consideration given to the elapsed time from the time point at which the exhaust gas sensor reaches the predetermined temperature. At the time of start of the internal combustion engine, the exhaust gas sensor in an inactive state is rapidly heated by the heater for the purpose of early start of use. At this time, the temperature of the exhaust gas sensor quickly rises to the target temperature, at the time of start of the internal combustion engine. Meanwhile, when the temperature of the exhaust gas sensor rises to the desorption start temperature or higher, the amount of the adsorbed species gradually decreases. More specifically, the physical phenomenon in which the adsorbed species are desorbed, and thereafter, the adsorbed species are removed from the area around the exhaust gas sensor advances with the lapse of the time while the exhaust sensor is heated to the target temperature, at each time of start of the internal combustion engine. Thus, in the third invention, at the time of start of the internal combustion engine, the time is measured with the time point, at which the exhaust gas sensor temperature reaches the predetermined temperature set in advance which is the target temperature or lower, set as the starting point. The time is included in the basis of activation determination, and thereby, the advance extent of a series of physical phenomena relating to desorption of the adsorbed species can be reflected in the activation determination. Thereby, use of the exhaust gas sensor output including a large effect of the adsorbed species can be suppressed.

According to the fourth invention, the situation can be suppressed, in which the exhaust gas sensor output is used though the effect of the adsorbed species remains, when the exhaust gas sensor activation is determined based on the temperature of the exhaust gas sensor. More specifically, according to the fourth invention, even when the temperature of the exhaust gas sensor reaches the activation temperature, if the elapsed time after the time of the desorption start temperature is shorter than the predetermined time, the exhaust gas sensor is prohibited from being determined as being in the activation state. More specifically, until the time set in advance elapses, the state of prohibiting use of the exhaust gas sensor output can be ensured. As a result, the situation can be suppressed, in which the exhaust gas sensor output is used though the effect of the adsorbed species remains.

According to the fifth invention, even if the exhaust gas sensor reaches the activation temperature, the exhaust gas sensor is not instantly determined as being in the activation state. According to the knowledge of the inventor of the present application, it is conceivable that actually in many cases, the effect of the adsorbed species remains even after the exhaust gas sensor reaches the activation temperature. The inventor of the present application has found out that it is effective to provide the time period of prohibition of use of the exhaust gas sensor output beyond the time at which the exhaust gas sensor reaches the activation temperature while there is the demand for early use of the exhaust gas sensor output. Thereby, the situation can be reliably prevented, in which the exhaust gas sensor output with the effect of adsorbed species remaining is used.

According to the sixth invention, the time point at which the exhaust gas sensor reaches the activation temperature is set as a starting point, and after the predetermined time further elapses from the time point, the exhaust gas sensor is determined as being in the activation state. According to the knowledge of the inventor of the present application, actually in many cases, the effect of the adsorbed species remains even after the exhaust gas sensor reaches the activation temperature. The inventor of the present application has found out that it is effective to introduce the time in which the exhaust gas sensor is not determined as being in the activation state (in other words, a waiting time) on purpose after the exhaust gas sensor reaches the activation temperature, while there is the demand for early use of the exhaust gas sensor output. Thereby, the situation can be reliably prevented, in which the exhaust gas sensor output with the effect of the adsorbed species remaining is used.

According to the seventh invention, both of whether or not the time is past the time point when the exhaust gas sensor reaches the activation temperature by heating by the heater, and whether or not such a time that the output shift of the exhaust gas sensor due to the adsorbed species is substantially eliminated has elapsed can be determined based on comparison of the elapsed time and the predetermined time. Consequently, according to the sixth invention, the determination that the exhaust gas sensor reaches the activation temperature, and the determination of elimination of the effect of the output shift due to the adsorbed species can be collectively performed by time measurement.

According to the eighth invention, the value of the predetermined temperature for determining the starting point of counting the time can be set from the temperature range in which the desorption temperatures of the adsorbed species mainly have a distribution. More specifically, the exhaust gas includes a plurality of components with different desorption temperatures when they become the adsorbed species. According to the knowledge of the inventor of the present application, in the case of gasoline, those with low desorption temperatures among adsorbed species (more specifically, HC of relatively low molecules and oxygen) has a distribution of the desorption temperatures in the temperature zone of about 300° C. or higher. Meanwhile, in the case of gasoline, those with high desorption temperatures among the adsorbed species (more specifically, HC of relatively high molecules) has a distribution of the desorption temperatures within the temperature zone of about 700° C. or lower. According to the eighth invention, the value of the predetermined temperature can be properly selected in accordance with the temperature range in which the desorption temperatures of the adsorbed species in gasoline are distributed.

According to the ninth invention, an impedance and an admittance are used as the physical amount having a correlation with the temperature of the exhaust gas sensor. At this time, in order that these electrical physical amounts reach high precision to a certain extent, the temperature of the exhaust gas sensor rises to a certain extent. Thus, in the ninth invention, with this point taken into consideration, a predetermined temperature for determining the starting point of time measurement from the temperature zone of 400° C. or higher. Thereby, time measurement can be performed with high precision.

According to the tenth invention, the predetermined time in the aforementioned fourth to sixth inventions can be changed in accordance with the fuel property. Thereby, the variation of the extent of the exhaust gas sensor output shift due to difference in the fuel property can be reflected in the predetermined time in the aforementioned fourth to sixth inventions.

According to the eleventh invention, with consideration given to the point that the length of the time period of the output shift to the rich side changes in accordance with the rich side peak, the predetermined time in the aforementioned fourth to sixth inventions can be changed in accordance with the rich side peak. As a result, the predetermined times in the aforementioned fourth to sixth inventions can be changed to the lengths which are neither too long nor too short.

According to the twelfth invention, the predetermined times in the aforementioned fourth to sixth inventions can be changed in accordance with the amount of the adsorbed species. As a result, the predetermined times in the aforementioned fourth to sixth inventions can be changed to the lengths which are neither too long nor too short.

According to the thirteenth invention, each kind of amount having a correlation with the amount of the adsorbed species is used, and thereby, the predetermined times in the aforementioned fourth to sixth inventions can be set to be longer as the amount of the adsorbed species is larger.

According to the fourteenth invention, when it can be determined that the effect of the adsorbed species is small enough to be ignored, the exhaust gas sensor can be determined as being in the activation state at the time point at which the exhaust gas sensor reaches the activation temperature. Therefore, when the effect of the adsorbed species can be ignored, activation determination of the exhaust gas sensor can be quickly performed correspondingly.

According to the fifteenth invention, the integrated air amount, the element temperature or the element admittance is measured, whereby it can be determined that the effect of the adsorbed species is sufficiently removed from the output of the exhaust gas sensor.

According to the sixteenth invention, at the time of start of the internal combustion engine, various harmful effects which are brought about by the sensor output shift due to the adsorbed species, for example, degradation of air-fuel ratio controllability, the adverse effect on drivability and the like can be suppressed.

According to the seventeenth invention, determination of the activation state can be properly performed for a critical current type exhaust gas sensor in which the effect of the output shift due to adsorbed species is large.

BRIEF DESCRIPTION OF DRAWINGS

FIG. 9 shows one example of a map specifying a target holding time TWACT corresponding to a cooling water temperature THWI.

FIG. 11 shows one example of a map specifying a target holding time TIACT corresponding to an impedance value TIMPI.

FIG. 13 shows one example of a map specifying a target holding time TAFPACT corresponding to rich side peak AFBACTP.

Figure 1:
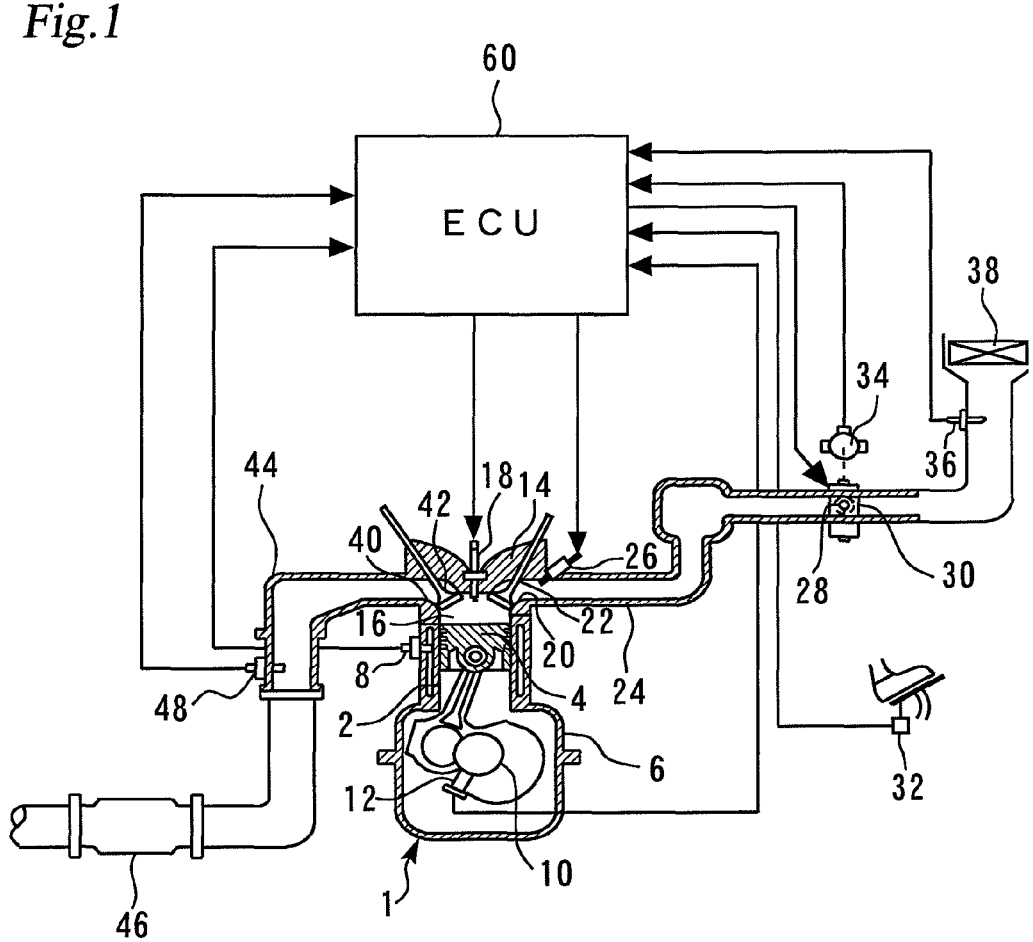
FIG. 1 is a view for describing a system configuration of a first embodiment of the present invention.

REFERENCE SIGNS LIST 1 an internal combustion engine
8 a cooling water temperature sensor
26 an injector
44 an exhaust passage
46 a catalyst
48 an air-fuel ratio sensor
50 a sensor element section
51 a detecting element
52 a measurement electrode
53 an atmosphere-side electrode
54 a porous diffusion resistance layer
57 a heater
70 a fuel tank
72 fuel piping
74 a fuel property sensor

DESCRIPTION OF EMBODIMENTS

First Embodiment

Description of the System Configuration of the First Embodiment

FIG. 1 is a view for describing a system configuration of a first embodiment of the present invention. A system of the present embodiment includes an internal combustion (Hereinafter, also referred to as "an engine".) 1. The internal combustion engine 1 has a plurality of cylinders 2, and FIG. 1 shows only one cylinder out of them.

The internal combustion engine 1 includes a cylinder block 6 which internally has a piston 4. The cylinder block 6 is provided with a cooling water temperature sensor 8 which detects a cooling water temperature THWI of the internal combustion engine 1. The piston 4 is connected to a crankshaft 10 via a crank mechanism. A crank angle sensor 12 is provided in the vicinity of the crankshaft 10. The crank angle sensor 12 is configured to detect a rotational angle (Hereinafter, referred to as "a crank angle".) CA of the crankshaft 10.

A cylinder head 14 is assembled to a top portion of the cylinder block 6. A space extending from a top surface of the piston 4 to the cylinder head 14 forms a combustion chamber 16. The cylinder head 14 is provided with an ignition plug 18 which ignites an air-fuel mixture in the combustion chamber 16.

The cylinder head 14 includes an intake port 20 which communicates with the combustion chamber 16. An intake valve 22 is provided in a connection portion of the intake port 20 and the combustion chamber 16. An intake passage 24 is connected to the intake port 20. The intake passage 24 is provided with an injector 26 which injects a fuel to a vicinity of the intake port 20.

A throttle valve 28 is provided upstream of the injector 26. The throttle valve 28 is an electronically controlled valve which is driven by a throttle motor 30. The throttle valve 28 is driven based on an accelerator opening degree AA which is detected by an accelerator opening degree sensor 32. A throttle opening degree sensor 34 which detects a throttle opening degree is provided in a vicinity of the throttle valve 28.

A hot wire air flow meter 36 is provided upstream of the throttle valve 28. The air flow meter 36 is configured to detect an intake air amount Ga. An air cleaner 38 is provided upstream of the air flow meter 36.

Further, the cylinder head 14 includes an exhaust port 40 which communicates with the combustion chamber 16. An exhaust valve 42 is provided in a connection portion of the exhaust port 40 and the combustion chamber 16. An exhaust passage 44 is connected to the exhaust port 40. The exhaust passage 44 is provided with an exhaust purifying catalyst (Hereinafter, referred to as "a catalyst".) 46 which purifies an exhaust gas. A critical current type air-fuel ratio sensor 48 is provided upstream of the catalyst 46. The air-fuel ratio sensor 48 has a sensor element section 50 as shown in FIG. 2.

Figure 2:
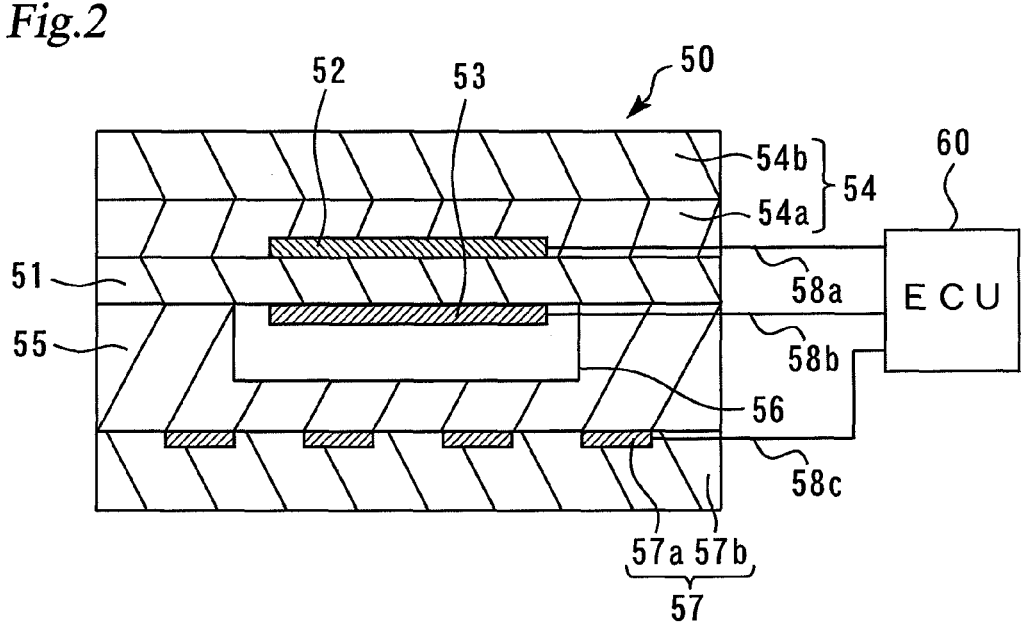
FIG. 2 is a sectional view showing a sensor element section 50 of an air-fuel ratio sensor 48.

FIG. 2 is a sectional view showing the sensor element section 50 of the air-fuel ratio sensor 48. The sensor element section 50 has a solid electrolyte layer as a detecting element 51. The solid electrolyte layer 51 is formed from a partially stabilized zirconia, and has oxygen ion conductivity. A measurement electrode 52 is provided on one surface of the solid electrolyte layer 51. Further, an atmosphere-side electrode (also referred to as "reference gas side electrode") 53 is provided on the other surface of the solid electrolyte layer 51. The measurement electrode 52 and the atmosphere-side electrode 53 are both formed from white gold or the like, and are respectively connected to an ECU 60 which will be described later through leads 58a and 58b.

Further, a porous diffusion resistance layer 54 is formed on one surface of the solid electrolyte layer 51. The porous diffusion resistance layer 54 covers the measurement electrode 52 and has a gas permeable layer 54a for introducing an exhaust gas to the measurement electrode 52, and a gas shut-off layer 54b which suppresses permeation of an exhaust gas.

The gas permeable layer 54a and the gas shutoff layer 54b are formed from ceramics such as alumina and zirconia, and differ from each other in the average pore size and porosity.

An atmosphere introduction duct 55 is formed on the other surface of the solid electrolyte layer 51. The atmosphere introduction duct 55 has an atmosphere chamber (also referred to as "reference gas chamber") 56 at an upper portion. The above described atmosphere-side electrode 53 is disposed in the atmosphere chamber 56. The atmosphere introduction duct 55 is formed from highly thermal conductive ceramics such as alumina. A heater 57 is provided on an undersurface of the atmosphere introduction duct 55. The heater 57 has a plurality of heat generators 57a which generate heat by energization, and an insulating layer 57b which covers the heat generators 57a. The heat generator 57a is connected to the ECU 60 via a lead 58c.

The sensor element section 50 having such a configuration can detect an oxygen concentration by a linear characteristic, and can output the critical current corresponding to the oxygen concentration to the ECU 60. The air-fuel ratio sensor output (critical current) has a correlation with the air-fuel ratio of an exhaust gas. More specifically, as the air-fuel ratio of the exhaust gas shifts to the lean side, the critical current increases, whereas as the air-fuel ratio of the exhaust gas shifts to the rich side, the critical current decreases.

Further, an admittance value As of the detecting element 51 has a correlation with the temperature of the detecting element 51. With use of this point, in the present embodiment, the temperature of the air-fuel ratio sensor 48 is measured based on the admittance value As of the detecting element 51.

Further, the system of the present embodiment includes the ECU (Electronic Control Unit) 60 as the control device. The ignition plug 18, the injector 26, the throttle motor 30 and the like are connected to an output side of the ECU 60. The cooling water temperature sensor 8, the crank angle sensor 12, the accelerator opening degree sensor 32, the throttle opening degree sensor 34, the air flow meter 36, the air-fuel ratio sensor 48 and the like are connected to an input side of the ECU 60.

The ECU 60 calculates an engine speed NE based on the output of the crank angle sensor 12. Further, the ECU 60 calculates an engine load KL based on the accelerator opening degree AA or the like which is detected by the accelerator opening degree sensor 32. The ECU 60 determines a fuel injection amount based on the engine speed NE, the engine load KL and the like. Further, the ECU 60 also includes a timer function of counting a time.

[Effect of Adsorbed Species]

It is known that exhaust gas components adsorb on the electrode section and the like of the exhaust gas sensor while an internal combustion engine stops. In the case of the first embodiment, exhaust gas components (HC which is an unburned component, $H_2O$ or $O_2$) adsorb onto the measurement electrode 52 of the sensor element section 50 while the internal combustion engine 1 stops. Further, exhaust gas components adsorb onto the surfaces of various porous ceramics structure sections of the air-fuel ratio sensor 48. Hereinafter, the exhaust gas components which adsorb onto the air-fuel ratio sensor 48 will be also generically referred to as "adsorbed species".

When the internal combustion engine 1 is started, energization of the heater 57 is started, and the temperature of the sensor element section 50 rises. When the temperature of the sensor element section 50 exceeds a specific temperature zone, adsorbed species start to be desorbed from the surface of the measurement electrode 52, and various reactions start to be active on the surface. On this occasion, $H_2$ which is a reducing substance is generated on the surface of the measurement electrode 52, or the reaction site with oxygen on the measurement electrode 52 decreases due to the presence of the adsorbed species, whereby the output of the air-fuel ratio sensor 48 temporarily shifts to a rich side. On the contrary, $O_2$ increases on the surface of the measurement electrode 52, whereby the output of the air-fuel ratio sensor 48 temporarily shifts to a lean side. When desorption of the adsorbed species advances with a rise in the temperature of the sensor element section 50, a shift to the rich side and a shift to the lean side of the sensor output are finally eliminated.

Figure 3:
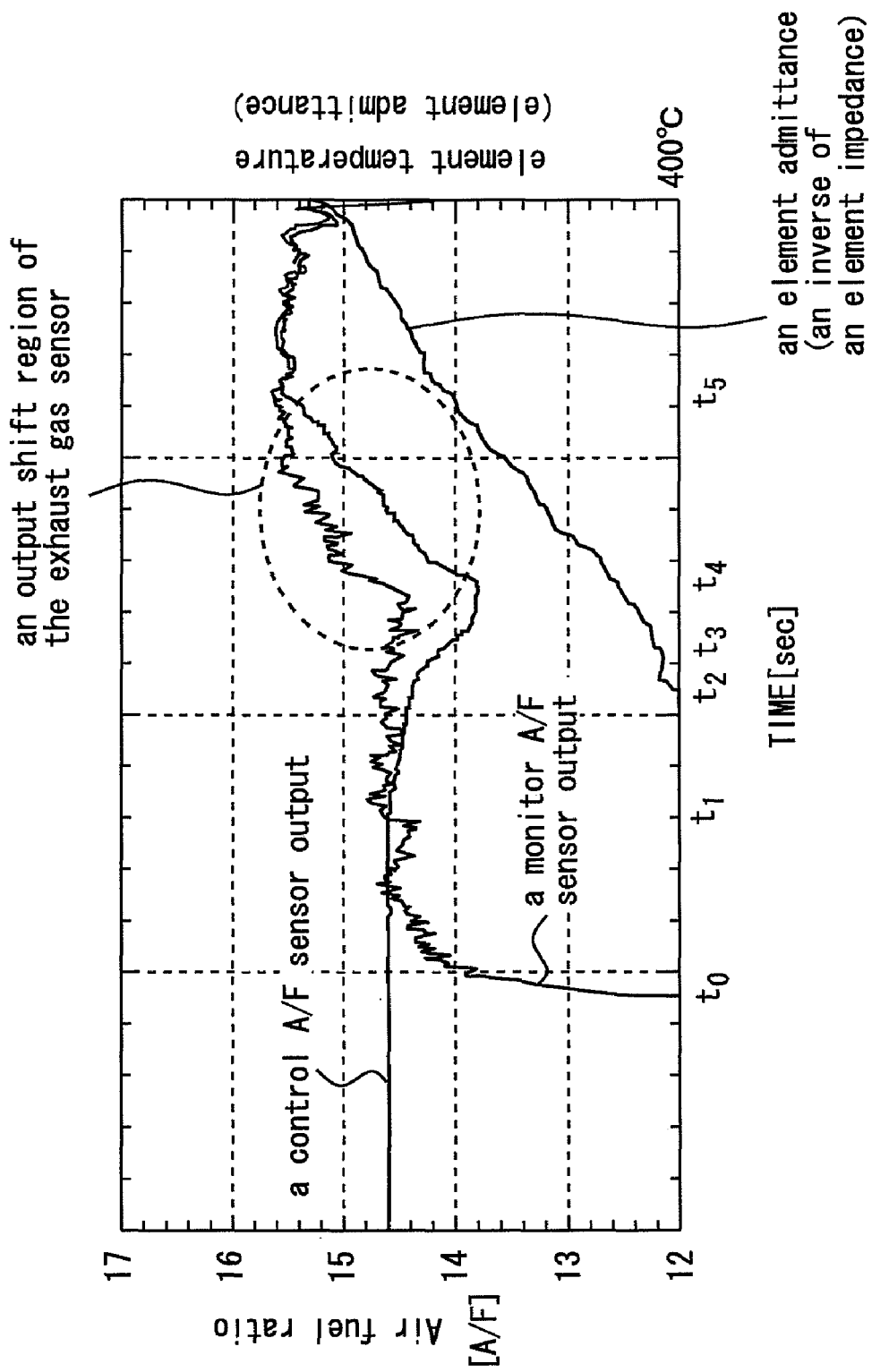
FIG. 3 is a diagram illustrating an effect of an output shift of an air-fuel ratio sensor 48 during warming-up.

FIG. 3 is a diagram illustrating the effect of the output shift of the air-fuel ratio sensor 48 during warming-up. FIG. 3 shows the result of the experiment which was performed by the inventor of the present application. FIG. 3 shows a monitor A/F sensor output, a control A/F sensor output, and an element admittance respectively by the solid lines. A control A/F sensor is an A/F sensor which is prepared in imitation of an ordinary A/F sensor which is disposed in the exhaust passage of an internal combustion engine. The monitor A/F sensor is an A/F sensor which is prepared for accurately monitoring the air-fuel ratio of the exhaust gas which flows toward the control A/F sensor. In this experiment, the control A/F sensor is heated to the activation temperature by a heater in imitation of the situation of the warming-up operation at the time of start. The value of the element admittance in FIG. 3 has a correlation with the temperature of the control A/F sensor. Meanwhile, the monitor A/F sensor is always kept at the activation temperature. More specifically, the exhaust gas with the air-fuel ratio indicated by the monitor A/F sensor output flows to the side of the control A/F sensor. The control A/F sensor is brought into the state in which the aforementioned effect of adsorbed species can be generated (the state in which adsorbed species are sufficiently adsorbed by being left standing for a sufficient time after the internal combustion engine stops).

FIG. 3 will be described along the time lapse from a time $t_0$ to $t_5$. First, from the time $t_0$, supply of the exhaust gas to the control A/F sensor is started. At this point of time, the control A/F sensor has not reached the activation temperature yet though heating by the heater is performed, and the output value fixedly indicates stoichiometry. Thereafter, when the time reaches a time $t_1$, the control A/F sensor output starts to shift to the rich side gradually. At this point of time, the value of the element admittance is about 300° C. though it does not appear in the graph of FIG. 3. When the time reaches a time $t_2$, the value of the element admittance appears in the graph of FIG. 3. At the point of the time $t_2$, the control A/F sensor is at 400° C. The measurement precision of the element admittance becomes sufficiently high in the temperature range of 400° C. or more, and therefore, FIG. 3 shows the measurement values from 400° C. or more.

Thereafter, from the time around a time $t_3$, the output of the control A/F sensor starts to shift to the rich side rapidly. In contrast with this, the output of the monitor A/F sensor indicates a value near stoichiometry. It is found out that at the time around the time $t_3$, the effect of the adsorbed species which adsorb on the control A/F sensor starts to be activated. Thereafter, at a time $t_4$, the shift of the output of control A/F sensor to the rich side reaches the peak. At a time $t_4$ and thereafter, the output of the control A/F sensor gradually returns to the lean side. Finally, at a time $t_5$, the output of the control A/F sensor corresponds to the output of the monitor A/F sensor. It is conceivable that at this point of time, the effect due to the adsorbed species is completely eliminated.

Operation of the First Embodiment

In general, there is a demand for early start of air-fuel ratio control (feedback control) using an exhaust gas sensor output at the time of start of an internal combustion engine. In the internal combustion engine 1, it is also desirable to make the output of the air-fuel ratio sensor 48 usable early and to enable air-fuel ratio feedback control to start as early as possible.

In general, when the temperature of the exhaust gas sensor rises to the activation temperature, the output characteristic of the exhaust gas sensor itself becomes stable. Therefore, if the air-fuel ratio sensor 48 reaches the activation temperature, preparation of the air-fuel ratio sensor 48 is considered to be completed in regard with the temperature condition. Further, it is conventionally considered that when the exhaust gas sensor reaches the temperature around the activation temperature (or, if the exhaust gas sensor reaches a high temperature to a certain extent, though it is lower than the activation temperature), the effect of adsorbed species is sufficiently eliminated. Therefore, it is conceivable that in the sensor activation determination according to the prior art, the air-fuel ratio sensor 48 is determined as being in the activation state at the point of time when the air-fuel ratio sensor 48 reaches the activation temperature.

However, the inventor of the present application has found out that the effect of adsorbed species sometimes remains even after the exhaust gas sensor reaches the activation temperature, that is, the effect of the adsorbed species sometimes still remains even if the exhaust gas sensor reaches a sufficiently high temperature. In concrete, the control A/F sensor can reach the activation temperature before the time $t_5$ in FIG. 3 in some cases. Even if the output precision of the air-fuel ratio sensor 48 becomes sufficient, the sensor output includes an error due to the effect of adsorbed species when the effect of the adsorbed species remains. As a result, accurate measurement of the exhaust gas air-fuel ratio is inhibited. It is not preferable to start the air-fuel ratio control using the output of the air-fuel ratio sensor 48 without consideration of such a situation.

Thus, in view of such an effect of adsorbed species, the inventor of the present application determines the activation state of the air-fuel ratio sensor 48 based on not only whether or not the air-fuel ratio sensor 48 reaches the activation temperature, but also whether or not the effect of the adsorbed species is sufficiently removed from the output of the air-fuel ratio sensor 48. In other words, the air-fuel ratio sensor 48 is determined as being in the active state when the following two conditions are satisfied.

(i) The air-fuel ratio sensor 48 reaches the activation temperature, and the output characteristic of the air-fuel ratio sensor 48 is stable.

(ii) The effect of adsorbed species is sufficiently removed from the output of the air-fuel ratio sensor 48.

The inventor of the present application has reached the technique of determining the establishment of the condition of the above described (ii) by measuring the time while warming up the air-fuel ratio sensor 48 by the heater 57. More specifically, in the present embodiment, the air-fuel ratio sensor 48 is determined as being in the activation state after a preset time (hereinafter, also referred to as "target holding time", and also described as "Te") elapses, after the temperature of the air-fuel ratio sensor 48 reaches the predetermined temperature (hereinafter, also described as T1, and T1=500° C. in the present embodiment). More specifically, unless a time Te does not elapse after the air-fuel ratio sensor 48 reaches the temperature T1, the air-fuel ratio sensor 48 is not determined as being in the activation state even if the temperature of the air-fuel ratio sensor 48 reaches the activation temperature.

(Setting of the Temperature T1)

In the present embodiment, the temperature T1 is set from the following viewpoint. Adsorbed species include various kinds of species such as HC and $O_2$. The respective adsorbed species start to be desorbed from the surface of the measurement electrode 52 when the temperature reaches the specific temperature. More specifically, the individual adsorbed species include peculiar temperatures (hereinafter, also referred to as "desorption temperatures") at which the adsorbed species start to be desorbed from the surface of the measurement electrode 52. At the point of time when the temperature of the air-fuel ratio sensor 48 reaches the lowest temperature of these desorption temperatures, desorption of the adsorbed species begins. Hereinafter, the temperature at which desorption of the adsorbed species from the air-fuel ratio sensor 48 starts, in other words, the lowest temperature of the adsorption temperatures will be also referred to as "desorption start temperature".

An exhaust gas includes a plurality of components which differ from one another in the desorption temperature at the time when they become adsorbed species. According to the knowledge of the inventor of the present application, in gasoline, the adsorption temperatures of the components with low adsorption temperatures (more specifically, relatively low-molecular HC and oxygen) out of the adsorbed species have a distribution in the temperature zone of about 300° C. or higher. Meanwhile, in gasoline, the desorption temperatures of the components (more specifically, relatively high-molecular HC) with high desorption temperatures among the adsorbed species are almost within the temperature zone of 700° C. or lower. The inventor of the present application estimates that the desorption temperatures of the adsorbed species in gasoline are within the range of 300° C. to 700° C. inclusive with consideration given to the point that HCs with various numbers of molecules are included in the fuel. Further, according to the knowledge of the inventor of the present application, it is assumed that the measurement precision of the element admittance and the element impedance which is high to a certain extent can be ensured at a temperature of 400° C. or higher, and therefore, the temperature T1 is preferably set at 400° C. or higher from the viewpoint of precise measurement of the time Te. In the present embodiment, with these points taken into consideration, the temperature T1 is set at 500° C.

(Setting of the Target Holding Time Te)

The time Te is set in advance empirically or by simulation with the following points taken into consideration. In the present embodiment, the time at which the air-fuel ratio sensor 48 reaches the temperature T1, that is, 500° C. is set as a starting point of counting, and the time until the time (the time $t_5$ illustrated in FIG. 3) when the sensor output value sufficiently converges is specified in advance by experiment. The time is set as Te.

As repeatedly described, the inventor of the present application pays attention to the fact that the effect of adsorbed species can still remain even after the exhaust gas sensor reaches the activation temperature. According to the knowledge of the inventor of the present application, it is conceivable that there are actually many cases in which the effect of the adsorbed species remains even after the air-fuel ratio sensor 48 reaches the activation temperature. More specifically, the inventor of the present application has found out that even if a little time loss occurs until start of use of the sensor output after the air-fuel ratio sensor 48 reaches the activation temperature, setting the time Te to be long is effective in avoiding the effect of adsorbed species and favorably starting the internal combustion engine 1.

Thus, in the present embodiment, the length of the time Te is set to be the length which is past the time at which the air-fuel ratio sensor 48 reaches the activation temperature by the heater 57 at the time of start of the internal combustion engine 1. Te is preferably set as the time until the effect of the adsorbed species is eliminated from the output value of the air-fuel ratio sensor 48 and the output value of the air-fuel ratio sensor 48 is stabilized, after the air-fuel ratio sensor 48 reaches the temperature T1. More specifically, Te is preferably set as such a time that the output of the air-fuel ratio sensor 48 can be confirmed to be converged onto the actual air-fuel ratio of the exhaust gas including a variation. When it is considered to satisfy these conditions, Te is preferably set to be sufficiently long even if Te becomes long enough to be past the time at which the air-fuel ratio sensor 48 reaches the activation temperature. Thereby, the situation can be reliably prevented, in which the output of the air-fuel ratio sensor 48 with the effect of the adsorbed species still remaining is used.

At the time of setting the time Te, the following point is preferably taken into consideration. In order that the effect of the adsorbed species is sufficiently eliminated from the sensor output value, it is firstly necessary that desorption of the adsorbed species has sufficiently advanced. Further, it is necessary that the effect of the adsorbed species, which are desorbed, is sufficiently removed from the vicinity of the air-fuel ratio sensor 48 (more specifically, the vicinity of the sensor element section 50). In other words, it is necessary that the rich atmospheric gas or lean atmospheric gas which surrounds the sensor element section 50 after desorption of the adsorbed species is replaced with the exhaust gas which is exhausted by the internal combustion engine 1.

As described above, when the temperature of the air-fuel ratio sensor 48 exceeds the desorption start temperature, the adsorbed species which are adsorbed on the measurement electrode 52 and the like start to be desorbed in sequence of those with lower desorption temperatures. Thereafter, the amounts of the respective adsorbed species respectively decrease in accordance with the lapse of the time. As above, when the specific temperature which is the desorption start temperature or higher is set as the starting point of counting, the desorption process of the adsorbed species takes a time Te1 first. Apart from Te1, a time Te2 is present for replacement of a rich atmospheric gas and a lean atmospheric gas in accordance with the flow rate of the exhaust gas. Te is preferably set with the times Te1 and Te2 taken into consideration.

As the precondition, the first embodiment is applied to the situation in which the air-fuel ratio sensor 48 is sufficiently cooled after the internal combustion engine 1 stops, and the amount of adsorbed species is assumed to be large. More specifically, the target case is such that several hours or more, or the period of about a day or more has elapsed after the internal combustion engine 1 stops.

(Sensor Activation State Determination of the First Embodiment)

In the present embodiment, time measurement using the temperature T1 and the time Te which are set as described above is performed, and thereby, the activation state of the air-fuel ratio sensor 48 is determined at the time of start of the internal combustion engine 1. More specifically, in the first embodiment, while the heater 57 heats the sensor element section 50 at the time of start of the internal combustion engine, the admittance value As of the detecting element 51 is acquired as the physical amount which indicates a correlation with the temperature of the air-fuel ratio sensor 48. When the admittance value As rises to the value indicating that the temperature of the air-fuel ratio sensor 48 reaches the temperature T1, time measurement is started with that time as the starting point of counting.

After the time measurement is started, the air-fuel ratio sensor 48 is heated by the heater 57, and the temperature of the air-fuel ratio sensor 48 finally reaches the activation temperature (for example, 750° C. or the like). At this time, the aforementioned condition (i) is established. However, in the present embodiment, the time Te is set to be sufficiently long as described above. Accordingly, at this point of time, the elapsed time from the measurement start time does not exceed Te. Therefore, the determination that the air-fuel ratio sensor 48 is in the activation state is not made yet.

Thereafter, when the elapsed time from the measurement start time exceeds Te, it is determined that the aforementioned condition (ii) is established. More specifically, it is determined that the effect of the adsorbed species is sufficiently removed from the output of the air-fuel ratio sensor 48. At this point of time, the determination that the air-fuel ratio sensor 48 is in the activation state is made.

As above, according to the first embodiment, the time can be measured with the point of time at which the temperature of the air-fuel ratio sensor 48 reaches the temperature T1 as the starting point of counting. The elapsed time after reaching the desorption start temperature is included in the basis of activation determination, and thereby, the elimination degree of the effect of the adsorbed species can be reflected in the activation determination. Thereby, use of the sensor output including a large effect of the adsorbed species can be suppressed.

More specifically, according to the first embodiment, when the elapsed time after reaching the temperature T1 is shorter than the time Te, determination that the air-fuel ratio sensor 48 is in the active state is prohibited even if the air-fuel ratio sensor 48 (sensor element section 50) reaches the activation temperature. As a result, the prohibition state of use of the output of the air-fuel ratio sensor 48 can be ensured until the time Te elapses. As a result, the situation can be reliably suppressed, in which the output of the air-fuel ratio sensor 48 is used although a large effect of the adsorbed species remains.

Further, according to the present embodiment, the time Te is set to be the aforementioned sufficient length (such a length as to be past the time at which the air-fuel ratio sensor 48 reaches the activation temperature) in advance. Accordingly, even if the air-fuel ratio sensor 48 reaches the activation temperature, the air-fuel ratio sensor 48 is not determined as being in the activation state immediately. Like this, in the present embodiment, the period in which use of the output of the air-fuel ratio sensor 48 is prohibited is provided across the time at which the air-fuel ratio sensor 48 reaches the activation temperature on purpose, while there is the demand for early use of the output of the air-fuel ratio sensor 48. As a result, the situation can be reliably suppressed, in which the output of the air-fuel ratio sensor 48 is used although the effect of the adsorbed species remains.

Specific Processing of the First Embodiment

Figure 4:
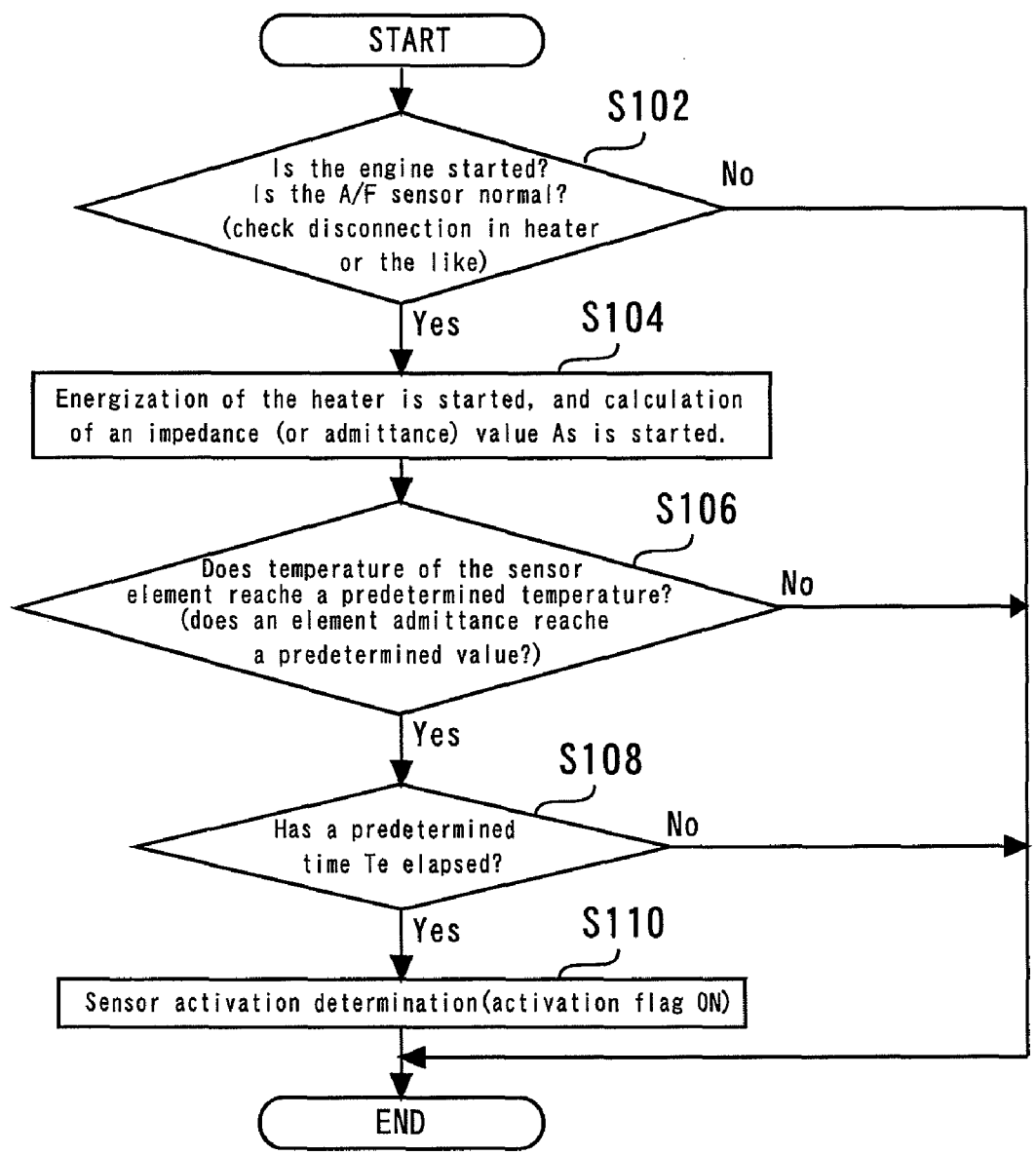
FIG. 4 is a flowchart of routines executed by an ECU 60 in the first embodiment.

Hereinafter, the specific processing according to the first embodiment will be described with use of FIG. 4. FIG. 4 is a flowchart of routines executed by the ECU 60 in the first embodiment, which is repeatedly executed at the time of start of the internal combustion engine 1. In the first embodiment, the routines are assumed to be executed when a period of about a day or more elapses after the internal combustion engine 1 stops.

After the routine shown in FIG. 4 is started, whether or not the engine is started, and whether or not the air-fuel ratio sensor 48 has an abnormality are determined (step 102). In step 102, it is determined whether or not a fracture in the sensor element section 50, and disconnection of the leads 58a, 58b and 58c, and the like occur. When it is determined that the air-fuel ratio sensor 48 has an abnormality in this step, countermeasures such as setting a sensor abnormality flag to "1", for example, can be taken. When the sensor abnormality flag is set to "1" like this, for example, a warning lamp (not illustrated) provided in the vehicle lights up. Thereby, the vehicle driver can recognize the sensor abnormality.

When establishment of the condition of step S102 is recognized, energization of the heater 57 is started, and calculation of the admittance value As is started (step S104). Thereby, warming-up of the air-fuel ratio sensor 48 is started, and the temperature of the air-fuel ratio sensor 48 is monitored.

Subsequently, it is determined whether or not the temperature of the sensor element section 50 reaches the temperature T1 (step S106). In this step, it is determined whether or not the admittance value As becomes an admittance value As1 or larger in the case of the temperature of the sensor element section 50 reaching the temperature T1. When the condition of this step is not established, the routines of this time end. When establishment of the condition of step S106 is recognized, the ECU 60 starts measurement of time, with the time in the step at the time of establishment of the condition as the starting point.

Thereafter, it is determined whether or not the time Te has elapsed after the ECU 60 starts the measurement (step S108). In this step, it is determined whether or not the measurement time of the ECU 60, that is, the elapsed time from the point of time at which the temperature of the sensor element section 50 reaches the temperature T1 is Te or more. Until establishment of the step is recognized, the routine shifts to END and temporarily ends, and thereafter, the present routines are repeatedly executed again.

When the condition of step S108 is established, it is determined that the air-fuel ratio sensor 48 is in the activation state (step S110). In this step, the ECU 60 turns on an air-fuel ratio sensor activation flag. Thereafter, the control of the internal combustion engine 1 shifts to the air-fuel ratio feedback control using the output of the air-fuel ratio sensor 48.

According to the above processing, the activation state of the air-fuel ratio sensor 48 can be determined with consideration given to the elapsed time from the point of time at which the temperature of the air-fuel ratio sensor 48 reaches the desorption start temperature as well as the temperature of the air-fuel ratio sensor 48. More specifically, the time can be measured with the point of time at which the temperature of the air-fuel ratio sensor 48 reaches the temperature T1 as the starting point. The elapsed time after the air-fuel ratio sensor 48 reaches the temperature T1 is included in the basis of the activation determination, whereby the degree of elimination of the effect of the adsorbed species can be reflected in the activation determination. Thereby, use of the output of the air-fuel ratio sensor 48 which includes a large effect of the adsorbed species can be suppressed. As a result, various harmful effects brought about by the shift of the sensor output, for example, degradation in air-fuel ratio controllability, the adverse effect on drivability and the like can be suppressed, at the time of start of the internal combustion engine 1.

In the aforementioned first embodiment, "determining means" in the aforementioned first invention is realized by a series of processing from step S104 to step S110 in the routines of FIG. 4.

In the above described first embodiment, "acquiring means" in the aforementioned second invention is realized by the processing of acquiring the admittance value As by the detecting element 51 from step 104 and the following steps in the routines of FIG. 4. "Temperature determining means" in the aforesaid second invention is realized by the processing of step S106 in the routines of FIG. 4. "Activation determining means" in the aforementioned second invention is realized by the processing of steps S108 and S110 in the routines of FIG. 4. Further, in the first embodiment, the temperature T1 corresponds to "predetermined temperature" in the aforementioned second invention.

Modified Example of the First Embodiment

First Modified Example

In the first embodiment, after the temperature T1 is set at 500° C., and the time Te elapses from the time at which the air-fuel ratio sensor 48 reaches the temperature T1, the air-fuel ratio sensor 48 is determined as being in the activation state. However, the present invention is not limited to this. T1 may be set at a temperature different from 500° C.

As described above, the desorption temperatures of adsorbed species differ in accordance with the kinds of the adsorbed species. For example, considering that HCs with various numbers of molecules are included in the fuel, the desorption temperatures of the adsorbed species are estimated to be within the range from 300° C. to 700° C. inclusive in general in the case of gasoline. More specifically, the desorption start temperature can be estimated to be 300° C. The temperature T1 of the first embodiment may be set at one temperature selected from the range from 300° C. to 700° inclusive, for example, 350° C., 400° C., 450° C., 550° C., 600° C. or 650° C. In that case, the time Te in the case of the selected temperature being set as the starting point of counting can be empirically determined in advance in accordance with the temperature.

Second Modified Example

The temperature T1 may be caused to correspond to the activation temperature of the air-fuel ratio sensor 48. More specifically, when the activation temperature of the air-fuel ratio sensor 48 is, for example, 750° C., the temperature T1 may be set at 750° C. In this modified example, the time point at which the air-fuel ratio sensor 48 reaches the activation temperature is set as the starting point, and after a predetermined time further elapses from the starting point, the air-fuel ratio sensor 48 is determined as being in the activation state.

As also described in the first embodiment, according to the knowledge of the inventor of the present application, it is conceivable that there are actually many cases in which the effect of adsorbed species remains even after the air-fuel ratio sensor 48 reaches the activation temperature. According to this modified example, the time in which the air-fuel ratio sensor 48 is not determined as being in the activation state (in other words, a waiting time until the sensor activation flag is turned on) is introduced on purpose after the air-fuel ratio sensor 48 reaches the activation temperature, while there is the demand for early use of the output of the air-fuel ratio sensor 48. Thereby, the situation can be reliably prevented, in which the output of the air-fuel ratio sensor 48 with the effect of the adsorbed species remaining is used.

Third Modified Example

In the first embodiment, the activation flag of the air-fuel ratio sensor 48 is turned on after the lapse of the time Te. In this case, "activation state of the exhaust gas sensor" as described in the present invention can be translated into "the state in which start of use of the exhaust gas sensor output is allowed" or "the state in which the exhaust gas sensor can really measure the air-fuel ratio of the exhaust gas accurately". More specifically, if the air-fuel ratio sensor 48 reaches the activation temperature, the air-fuel ratio sensor 48 can be said as being in the activation state as far as the temperature condition is concerned. However, in the present invention, the state in which the output of the air-fuel ratio sensor 48 can be used as the value indicating the exhaust gas air-fuel ratio is considered as the activation state of the air-fuel ratio sensor 48 as described above.

Accordingly, the following modification is also included in the technical scope of the present invention. For example, "activation temperature flag" relating to the temperature condition of the air-fuel ratio sensor 48, and "use permission flag" indicating that the output of the air-fuel ratio sensor 48 is usable for air-fuel ratio control are individually prepared. Alternatively, the activation temperature flag, and "adsorbed species effect flag" indicating that the effect of the adsorbed species is sufficiently removed from the output of the air-fuel ratio sensor 48 are individually prepared. The activation temperature flag is turned on at the time point at which the air-fuel ratio sensor 48 reaches the activation temperature. However, the use permission flag and the adsorbed species effect flag are turned off until the time Te elapses. Thereby, even if the air-fuel ratio sensor 48 is determined as being in the activation state with regard to the temperature condition, the air-fuel ratio sensor 48 is determined as not reaching "activation state" of the present invention in the time period in which the use permission flag and the adsorbed species effect flag are off. At least such a modified example is also included in the technical scope of the present invention.

Fourth Embodiment

In the first embodiment, the time Te is set to be long in view of the knowledge of the inventor of the present application. More specifically, the time period is provided, in which the air-fuel ratio sensor 48 is not determined as being in the activation state even after the air-fuel ratio sensor 48 reaches the activation temperature. However, the present invention is not limited to this, and the time Te can be set to be a proper length in accordance with the situation. More specifically, when the time until elimination of the effect of the adsorbed species is shorter than the time at which the air-fuel ratio sensor reaches the activation temperature, the time Te may be properly set to be short in accordance with this.

Fifth Modified Example

In the first embodiment, the admittance value As is used as the physical amount having a correlation with the temperature of the air-fuel ratio sensor 48. However, the present invention is not limited to this. The temperature of the air-fuel ratio sensor 48 may be measured according to the method which uses the element impedance. Further, estimation from the integrated value of the supply power to the heater 57 or the like may be performed. With regard to measurement of the temperature of the air-fuel ratio sensor, many known techniques are available, and therefore, further description will be omitted here.

Sixth Modified Example

In the first embodiment, the temperature T1 is set in the temperature zone of the desorption start temperature of the adsorbed species or higher. However, the present invention is not limited to this. As described as follows, the temperature T1 may be set at a temperature lower than the desorption start temperature (more specifically, a temperature lower than 300° C. when described in the first embodiment).

At the time of start of the internal combustion engine 1, the air-fuel ratio sensor 48 in the inactive state is rapidly heated by the heater 57 for the purpose of early start of use. At this time, the temperature of the air-fuel ratio sensor 48 quickly rises to a target temperature Ttgt (a specific temperature which is the same as or higher than the activation temperature), at the time of start of the internal combustion engine 1. The duty ratio of the heater 57 at the time of warming-up of the sensor is set at, for example, 100% or the like.

When the temperature of the air-fuel ratio sensor 48 rises to the desorption start temperature or higher, the amount of the adsorbed species gradually decreases. More specifically, at each time of start of the internal combustion engine, the physical phenomenon advances with the lapse of time, in which while the air-fuel ratio sensor 48 is heated to the target temperature, and the adsorbed species are desorbed and thereafter, are removed from the periphery of the air-fuel ratio sensor 48.

Thus, in the present modified example, at the time of start of the internal combustion engine 1, a time TTMP is measured with a predetermined temperature set in advance which is the target temperature Ttgt or lower as the starting point. As in the first embodiment, it is determined whether or not the elapsed time after start of the measurement exceeds the target holding time which is set in advance. The target holding time (hereinafter, described as "Tee") is set in advance from the same viewpoint as in the first embodiment, that is, at such a length that the effect of the output shift due to the adsorbed species is sufficiently eliminated. As in the first embodiment, the target holding time is stored in the ECU 60 as a map. When TTMP becomes Tee or more, the activation flag of the air-fuel ratio sensor 48 is turned on.

As above, time measurement is performed in the process of warming up the air-fuel ratio sensor, and the time is included in the basis of the activation determination, whereby the advance degree of a series of physical phenomena relating to the desorption of the adsorbed species can be reflected in the activation determination. Thereby, as in the first embodiment, use of the output of the air-fuel ratio sensor 48 which includes a large effect of the adsorbed species can be suppressed.

Seventh Modified Example

The air-fuel ratio sensor to which the present invention is applicable is not limited to the configuration of the air-fuel ratio sensor 48 of the first embodiment. For example, the present invention may be applied to a so-called two-cell type stacked air-fuel ratio sensor.

In recent years, the structure has been adopted, which makes the porous ceramics coating layer on the element surface thick to reinforce the protection function of the sensor. This is for the purpose of enhancing the strength of the element against the scattering condensed water in the exhaust pipe at the time of cold-start of an internal combustion engine.

In such a structure, the surface area of the ceramics coating layer is large, and therefore, the adsorption amount of the adsorbed species tends to be large correspondingly. In the air-fuel ratio sensor of such a type, the effect of the adsorbed species is highly likely to remain for a long period of time, and the significance of application of the present invention is high.

In the first embodiment, the activation determination for the air-fuel ratio sensor 48 is performed, but the present invention is not limited to this. The present invention also can be applied to an oxygen sensor, an NOx sensor for detecting the amount of NOx in the exhaust gas, and the like. The present invention can be applied to the sensor which is disposed in the exhaust gas passage of the internal combustion engine 1, is susceptible to the effect of the adsorbed species, and changes the output value in accordance with the air-fuel ratio and the components of the exhaust gas.

In the first embodiment, the case of the sensor output shifting to the rich side is mainly taken, but the present invention is not limited to this. For the situation in which the sensor output shifts to the lean side, the activation determination of the air-fuel ratio sensor can be performed as in the first embodiment by properly setting the temperature T1 and the target holding time Te.

Second Embodiment

Hereinafter, the second embodiment of the present invention will be described. The second embodiment includes the configuration of FIG. 1 such as the internal combustion engine 1 as in the first embodiment. The second embodiment differs from the first embodiment in the point of changing the time Te in accordance with the property of the fuel which is charged in the internal combustion engine 1. Hereinafter, the difference from the first embodiment will be mainly described, and the description of the same components as those in the first embodiment will be omitted or simplified.

Description of System Configuration of the Second Embodiment

Figure 5:
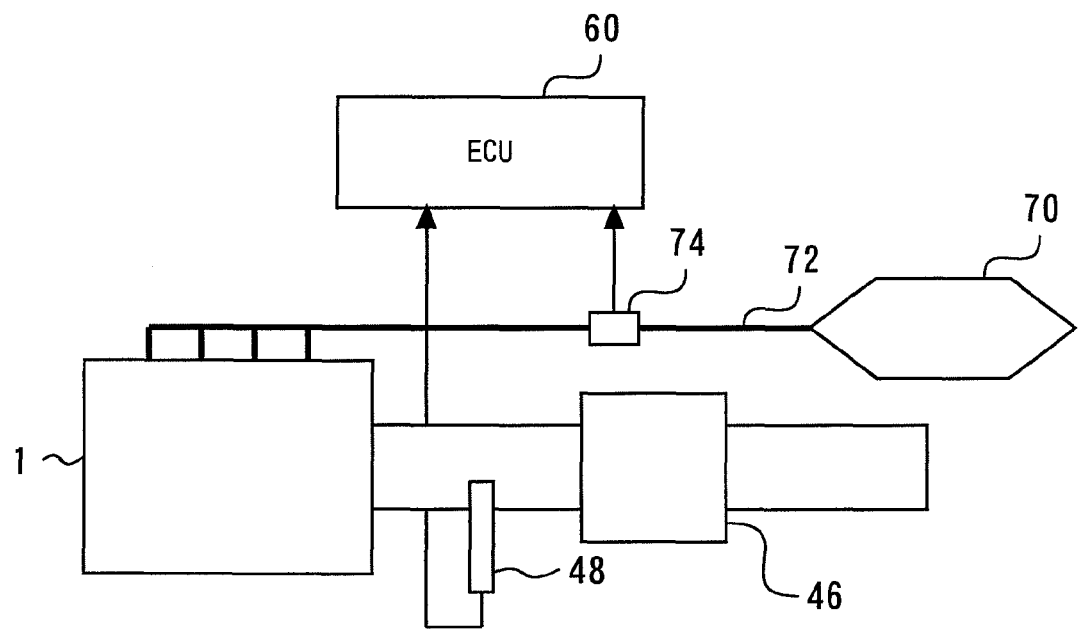
FIG. 5 shows a system configuration of a second embodiment.

FIG. 5 shows a system configuration of the second embodiment. A system of the second embodiment includes the internal combustion engine 1 (shown by being simplified), a catalyst 46, an air-fuel ratio sensor 48, and an ECU 60 as in the first embodiment. The other components of the first embodiment are assumed to be present as in FIG. 1 though not illustrated in FIG. 5.

The system of the second embodiment includes a fuel tank 70. The fuel in the fuel tank 70 is supplied to the injector 26 of the internal combustion engine 1 through fuel piping 72. A fuel property sensor 74 is disposed in the fuel piping 72. The fuel property sensor 74 issues the output corresponding to the property of the fuel in the fuel tank 70, and the output is inputted in the ECU 60.

Operation and Specific Processing of the Second Embodiment

The output shift in the process of warming-up at the time of start of the air-fuel ratio sensor 48 differs depending on the easiness of adsorption of the adsorbed species and the desorption temperature. Especially in FFV which uses an ethanol composite fuel, the degree of the output shift in the process of warming-up at the time of start tends to vary significantly as compared with the case of use of ordinary gasoline. Thus, in the second embodiment, with the tendency as described above taken into consideration, the values of the temperature T1 and the time Te in the first embodiment are changed in accordance with the fuel property.

Figure 6:
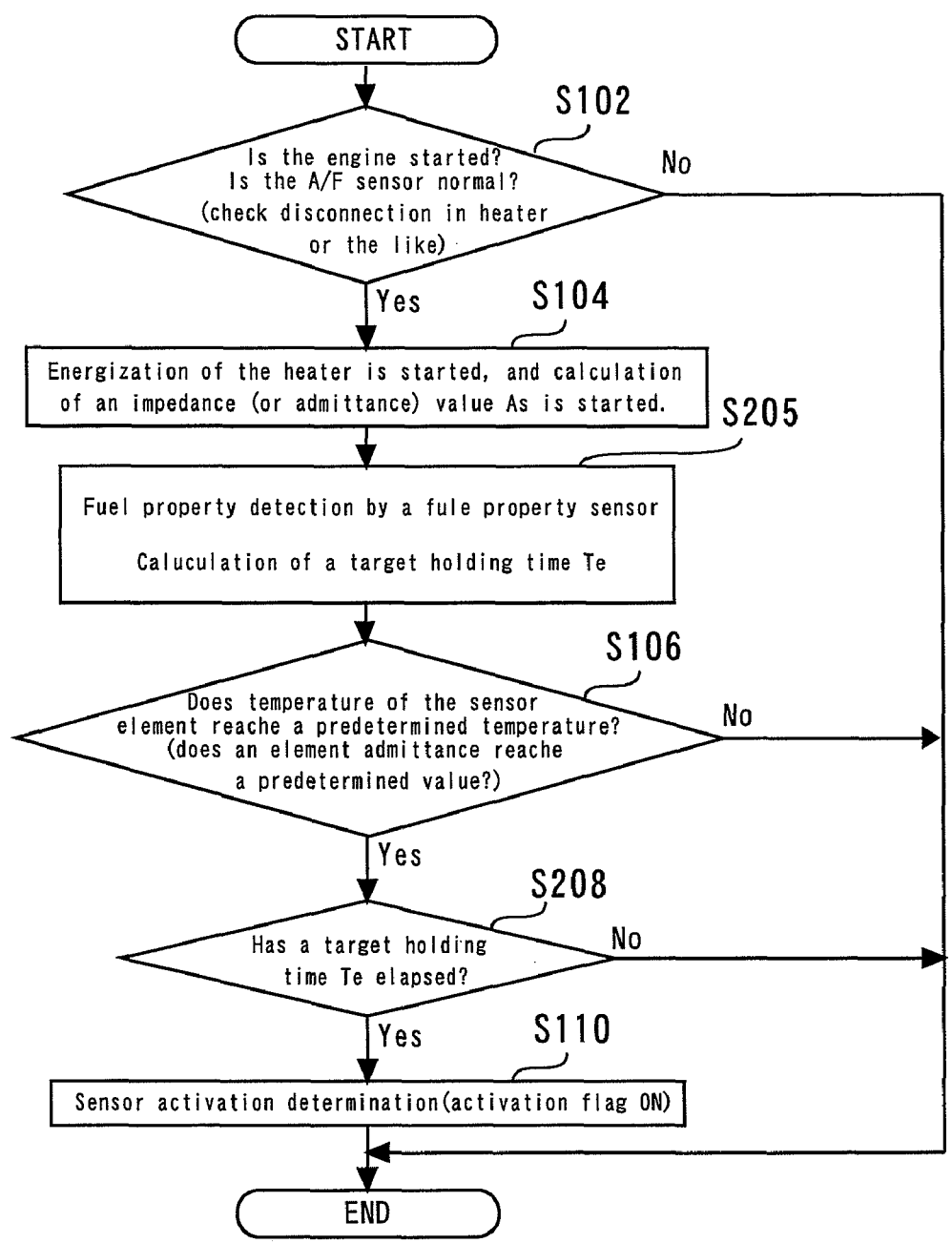
FIG. 6 is a flowchart of routines executed by the ECU 60 in the second embodiment.

FIG. 6 is a flowchart of routines executed by the ECU 60 in the second embodiment. The routines of FIG. 6 are assumed to be executed repeatedly under the same conditions as in the routines of FIG. 5 of the first embodiment. The routines of FIG. 6 include the same steps as in the routines of FIG. 5 except for the processing contents of steps S205 and S208. In the following description, the difference will be mainly described.

When the routines of FIG. 6 are started, the processing of steps S102 to S104 is executed as in the routines of FIG. 5. Thereafter, the process reaches step S205.

In step S205, the property of the fuel in the fuel tank 70 is acquired based on the fuel property sensor 74. Here, in the second embodiment, the map of the time Te corresponding to the property of the fuel to be charged is created in advance. More specifically, in accordance with the difference of the ethanol concentrations in the fuel, for example, the time Te is empirically determined in advance for each of fuels such as E0, E85 and E100. In step S205, the map of the time Te is referred to, and Te(1) which is the target holding time corresponding to the present fuel property I based on the fuel property sensor 74 is acquired.

Thereafter, in step S106, the time measurement of the ECU 60 is started as in the first embodiment, and thereafter, the process goes to step S208. In step S208, it is determined whether or not Te(I) which is obtained in step S205 has elapsed from the time of start of the time measurement in step S106. When Te(I) has elapsed thereafter, the process shifts to step S110, and the sensor activation flag is turned on. Thereafter, as in the first embodiment, the process shifts to air-fuel ratio feedback control.

As described above, according to the second embodiment, the time Te can be changed in accordance with the fuel property. Thereby, variation of the degree of the output shift of the air-fuel ratio sensor 48 due to the difference in the fuel property can be reflected in the time Te. As a result, the waiting time until the activation flag of the air-fuel ratio sensor 48 is turned on according to the time Te can be set without excess or deficiency.

The fuel property may be determined according to the output of the air-fuel ratio sensor 48 under operation of the previous time, and various estimation methods of the fuel properties may be used without being limited to the fuel property sensor 74. These methods are already known, and are not new matters, and therefore, the description of them will be omitted.

Third Embodiment

The third embodiment is predicated on the same system configuration and operation as those of the first embodiment. Hereinafter, the difference between the third embodiment and the first embodiment will be mainly described.

In the third embodiment, the sensor output is masked to be stoichiometry as in Japanese Patent No. 2008-138569 in the first embodiment. More specifically, the output of the air-fuel ratio sensor 48 is fixed to stoichiometry until the activation flag of the air-fuel ratio sensor 48 is turned on.

Here, at the moment at which the activation flag of the air-fuel ratio sensor 48 is turned on, masking is released, and the actual output of the air-fuel ratio sensor 48 is taken in. At this time, there is the fear of the output signal which is recognized as the output of the air-fuel ratio sensor 48 significantly changes discontinuously to the actual output from the stoichiometric output. Such a change is likely to be recognized as an air-fuel ratio variation by the control (ECU 60). Thus, in the third embodiment, for the purpose of preventing the effect, predetermined leveling processing (smoothing processing in the time direction) is performed for the output signal of the air-fuel ratio sensor 48 after the activation flag of the air-fuel ratio sensor 48 is turned on.

Figure 7:
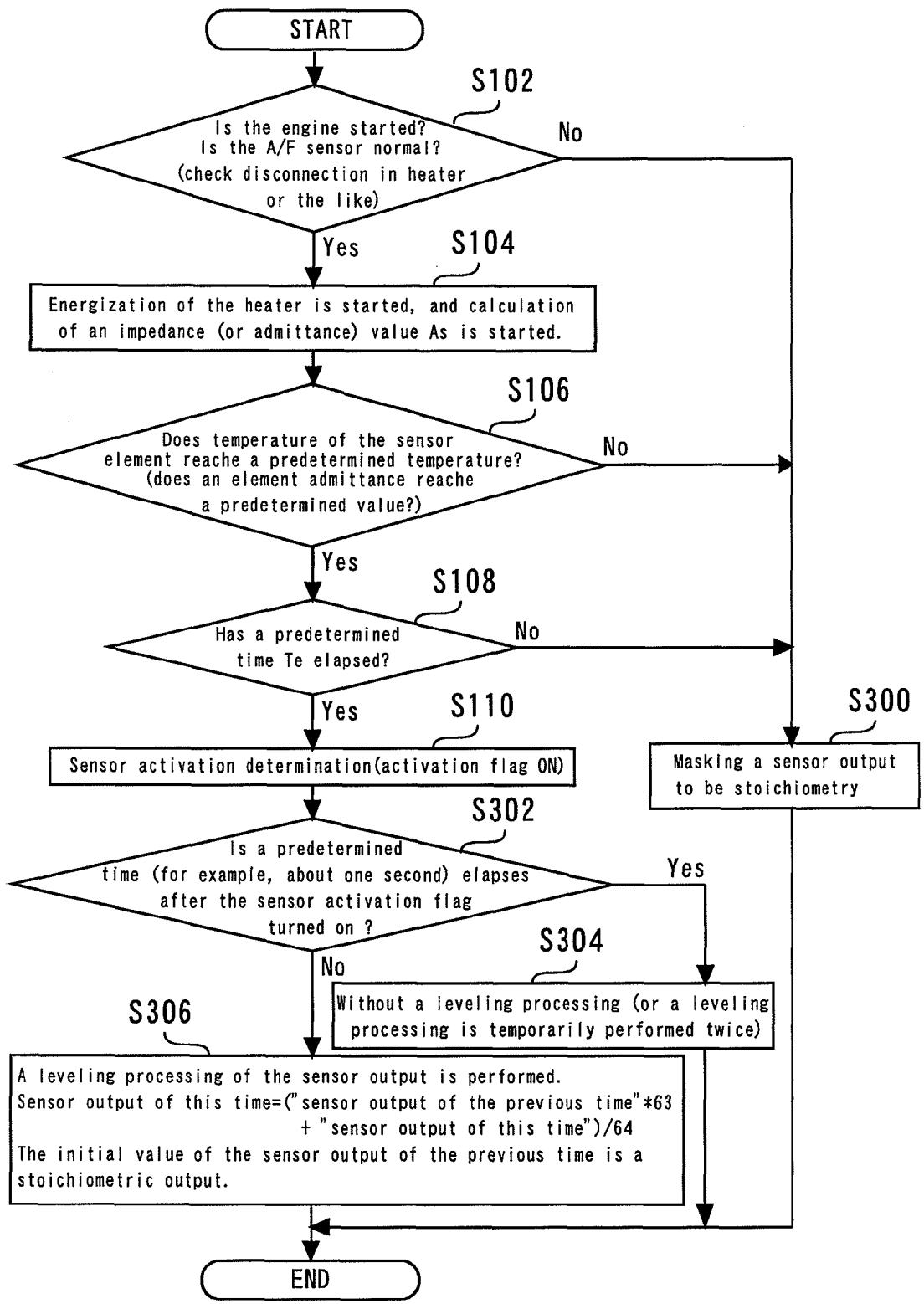
FIG. 7 is a flowchart of routines executed by the ECU 60 in a third embodiment.

FIG. 7 is a flowchart of routines executed by the ECU 60 in the third embodiment. The routines of FIG. 7 include the processing of steps S102 to S110 as in the routines of FIG. 5. The routines of FIG. 7 are the same as the flowchart of FIG. 5 except for the processing of steps S300, S302, S304 and S306.

In the routines of FIG. 7, the processing of steps S102 to S110 is executed as in the routines of FIG. 5. When the condition is not established in each of steps S102, S106 and S108, the output of the air-fuel ratio sensor 48 is masked to be stoichiometry in the processing of step S300.

When the process goes through the processing of step S110, and the activation flag of the air-fuel ratio sensor 48 is turned on, it is subsequently determined whether or not a predetermined time (for example, about one second) elapses after the sensor activation flag is turned on (step S302). When the condition of the step is denied, it is determined that the present time is immediately after the sensor activation flag is turned on, and the leveling processing of the sensor output is required. Subsequently, in step S306, the leveling processing of the sensor output is performed. In the third embodiment, the following signal processing is performed as an example.

Sensor output of this time=(sensor output of the previous time×63+sensor output of this time)/64

The initial value of the sensor output of the previous time is a stoichiometric output.

When establishment of the condition of step S302 is recognized, it is determined that a sufficient time elapses after the sensor activation flag is turned on. Therefore, the leveling processing of the sensor output is finished (or, the leveling processing is finally finished after the leveling processing is temporarily performed twice), and air-fuel ratio control is performed by using the actual output signal of the air-fuel ratio sensor 48.

As described above, according to the third embodiment, degradation of air-fuel ratio controllability which is feared at the time of start of use of the output of the air-fuel ratio sensor 48 can be suppressed.

Fourth Embodiment

Basic Concept of the Fourth Embodiment

Hereinafter, the fourth embodiment will be described on the precondition that the fourth embodiment has the same system configuration as the first embodiment, and can execute the similar operation. However, in the fourth embodiment, the temperature T1 is set to the activation temperature (in other words, the target temperature Ttgt of the heater 57) of the air-fuel ratio sensor 48, unlike the first to the third embodiments. Therefore, in the fourth embodiment, as in the aforementioned second modified example of the first embodiment, the target holding time functions as the waiting time after the air-fuel ratio sensor 48 reaches the activation temperature.

The amount of the adsorbed species (hereinafter, also described as "adsorption amount") which are adsorbed to the air-fuel ratio sensor 48 changes depending on the cooling situation of the air-fuel ratio sensor 48 after the internal combustion engine 1 stops. The adsorbed species are mainly the HC components and the like in the exhaust gas which are adsorbed onto the sensor element section 50 or the like under the situation in which the temperature of the air-fuel ratio sensor 48 lowers to about 300° C. or lower. If the adsorption amount differs, the length of the time in which the output shift of the air-fuel ratio sensor 48 due to the adsorbed species remains differs.

Here, the inventor of the present application pays attention to the following two tendencies.

(a) At the time of warming-up from the state of the air-fuel ratio sensor 48 being completely cooled (cooled to the room temperature or lower), the output shift remains for a long time even after the air-fuel ratio sensor 48 reaches the activation temperature.

(b) In the case of re-warming up from the state in which the air-fuel ratio sensor 48 is not so cooled after the engine stops at the previous time (for example, re-warming up within several hours after the internal combustion engine 1 stops), the output shift after the air-fuel ratio sensor 48 reaches the activation temperature is eliminated in a relatively short time.

Thus, in the fourth embodiment, the target holding time Te is changed based on the cooling situation of the air-fuel ratio sensor 48 with the aforementioned tendency taken into consideration. More specifically, in the fourth embodiment, based on the cooling water temperature THWI at the time of start of the internal combustion engine 1, the cooling situation of the air-fuel ratio sensor 48 is estimated, and the target holding time Te is changed.

Operation and Specific Processing of the Fourth Embodiment

Figure 8:
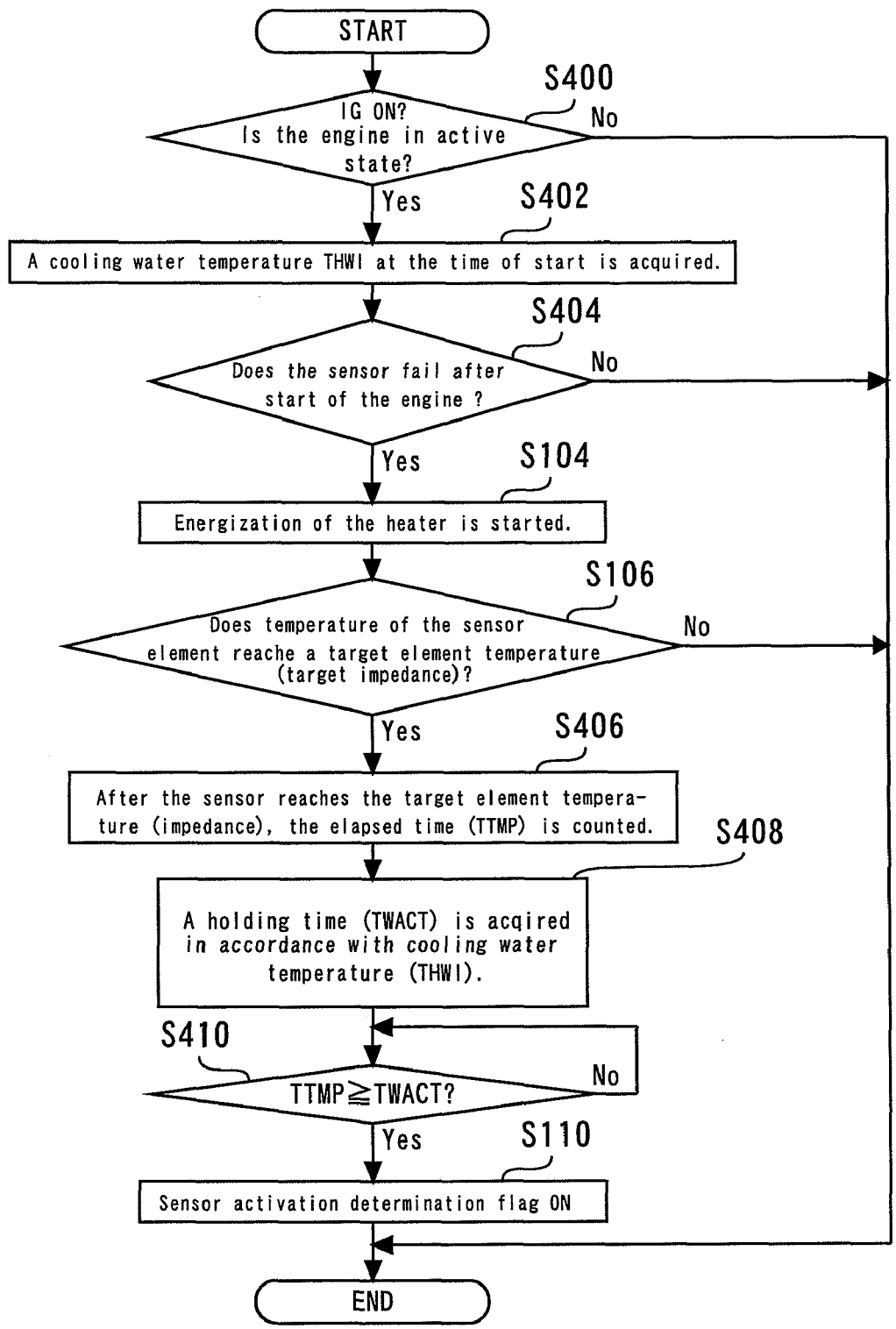
FIG. 8 is a flowchart of routines executed by the ECU 60 in a fourth embodiment.

FIG. 8 is a flowchart of routines executed by the ECU 60 in the fourth embodiment. The common steps to the flowchart of FIG. 5 are assigned with the same reference signs.

FIG. 9 shows a map which the ECU 60 refers to at the time of execution of the routines of FIG. 8. FIG. 9 shows one example of the map specifying the target holding time (described as TWACT in the fourth embodiment) corresponding to the cooling water temperature THWI. The map of FIG. 9 is set so that as the cooling water temperature THWI is higher, the target holding time TWACT becomes shorter. When the cooling water temperature THWI is sufficiently high (40° C. in the fourth embodiment), the target holding time TWACT is set to zero. The map is empirically created in advance.

In the routines of FIG. 8, after start of the sensor activation determination routine, it is firstly determined whether or not the ignition is on, that is, the engine is in the active state (step S400). When the condition of step S400 is established, then the cooling water temperature THWI at the time of start is acquired based on the output of the cooling water temperature sensor 8 (step S402). Subsequently, it is determined whether the air-fuel ratio sensor 48 fails after start of the engine (step S404). In this step, it is determined whether an abnormality is present in the air-fuel ratio sensor 48 as in the processing content of step S102 in the routines of FIG. 5 and the like. Thereafter, as in the routines of FIG. 5 and the like, the processing of steps S104 and S106 is executed.

After it is determined that the air-fuel ratio sensor 48 reaches the temperature T1 in step S106, the elapsed time is counted by the timer function which the ECU 60 has (step S406). In the fourth embodiment, the time counted here is described as TTMP.

After step S406, the map of FIG. 9 is subsequently referred to, and the target holding time TWACT corresponding to the cooling water temperature THWI acquired in step S402 is acquired (step S408).

Next, it is determined whether or not TTMP is TWACT or more (step S410). In this step, the process enters the loop processing until the elapsed time TTMP from the time when the air-fuel ratio sensor 48 reaches the temperature T1 exceeds the target holding time TWACT. In the fourth embodiment, the output of the air-fuel ratio sensor 48 is masked to be stoichiometry during this period of time. Thereafter, at the point of time when TTMP becomes TWACT or more, the process exits from the loop processing. The sensor activation flag is finally turned on in step S104, and the routines of this time end.

According to the above processing, the point that the length of the output shift time period changes in accordance with the cooling situation of the air-fuel ratio sensor 48 can be reflected in the target holding time. As a result, the target holding time can be changed to the length which is neither too long nor too short.

In place of the cooling water temperature, the intake air temperature, the oil temperature or the like at the time of start of the internal combustion engine 1 may be used.

Further, in the present embodiment, the map shown in FIG. 9 is created, but the present invention is not limited to this. For example, the time Te may be multiplied with the correction coefficient so that as the cooling water temperature THWI is higher, the target holding time becomes shorter.

Further, in the present embodiment, when the cooling water temperature at the time of start is high, it is determined that the adsorption amount of the HC component to the air-fuel ratio sensor 48 is almost absent, and the target holding time TWACT is set to zero. In this case, at the point of time when the temperature of the sensor element section 50 reaches the activation temperature, the sensor activation flag in step S110 is quickly turned on. However, the present invention is not limited to this, and a very short time to a certain extent may be ensured as the target holding time.

In the fourth embodiment, the temperature T1 is set as the activation temperature, but the temperature T1 may be properly set to a temperature of 500° C. or the like as in the first embodiment. In such a case, if the map is created, which reflects the point that the length of the output shift time period changes corresponding to the cooling situation of the air-fuel ratio sensor 48 as in the above description, the similar effect to that of the fourth embodiment can be obtained.

Fifth Embodiment

Basic Concept of the Fifth Embodiment

Hereinafter, the fifth embodiment will be described on the precondition that the fifth embodiment has the same system configuration as in the first embodiment, and can execute the similar operation. However, in the fifth embodiment, the temperature T1 is set to the activation temperature of the air-fuel ratio sensor 48 (in other words, the target temperature Ttgt of the heater 57) as in the fourth embodiment.

The fifth embodiment is common to the fourth embodiment in the point that the target holding time Te in the first embodiment is changed based on the cooling situation of the air-fuel ratio sensor 48. However, in the fifth embodiment, the target holding time Te is changed based on the temperature of the air-fuel ratio sensor 48 at the time of start of the internal combustion engine 1 unlike the fourth embodiment. In the fifth embodiment, as the physical amount having a correlation with the temperature of the air-fuel ratio sensor 48, the impedance of the detecting element 51 is used. In the fifth embodiment, the target holding time Te is also changed based on the two tendencies ((a) and (b)) described in the fourth embodiment.

Operation and Specific Processing of the Fifth Embodiment

Figure 10:
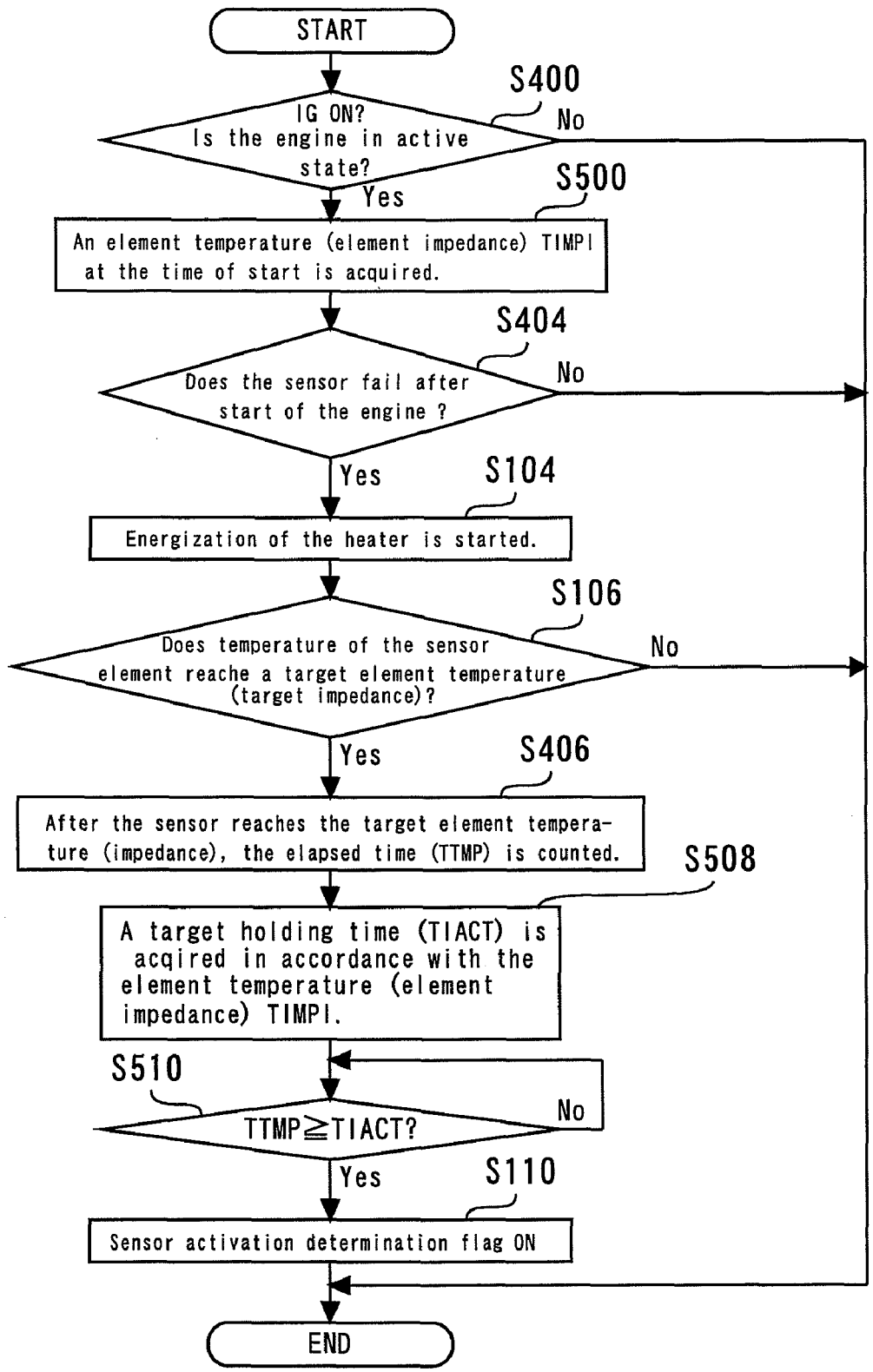
FIG. 10 is a flowchart of routines executed by the ECU 60 in a fifth embodiment.

Hereinafter, an operation of the fifth embodiment will be described with the specific processing in the fifth embodiment. FIG. 10 is a flowchart of routines executed by the ECU 60 in the fifth embodiment. In the routines of FIG. 10, the routines of the same processing contents as in the routines described in the first to the fourth embodiments are assigned with the same reference signs.

FIG. 11 is a map which is stored in the ECU 60 in advance in the fifth embodiment. In the fifth embodiment, the relation of an impedance value TIMPI (or may be the admittance value As) of the detecting element 51 at the time of start of the internal combustion engine 1 and the time TIACT is empirically specified in the map as shown in FIG. 11. The map is specified so that as the impedance value TIMPI shows that the air-fuel ratio sensor 48 is at a higher temperature, the target holding time (described as TIACT in the fifth embodiment) becomes shorter.

In the routines of FIG. 10, the processing of step S400 is firstly executed as in the fourth embodiment. Thereafter, the processing of acquiring the impedance value TIMPI at the time of start is executed (step S500). The technique of obtaining the impedance value for obtaining the temperature of the air-fuel ratio sensor or the like is already known and is not a new matter. Therefore, the description of it will be omitted here. After execution of the processing of step S500, steps S404, S104 and S106 are executed in sequence, and count of TTMP is started in S406.

Subsequently, the map shown in FIG. 11 is referred to, and the target holding time TIACT is acquired in accordance with the value of TIMPI which is acquired in step S500 (step S508).

Next, it is determined whether or not TTMP becomes TIACT or more (step S510). In this step, the process enters the loop processing until the elapsed time from the time when the air-fuel ratio sensor 48 reaches the temperature T1 exceeds the target holding time. In the fifth embodiment, the output of the air-fuel ratio sensor 48 is also masked to be stoichiometry during this time period. Thereafter, the process exits from the loop processing at the point of time when TTMP becomes TIACT or more. Finally, the sensor activation flag is turned on in step S104, and the routines of this time end.

According to the above processing, the point that the length of the output shift time period changes in accordance with the cooling situation of the air-fuel ratio sensor 48 can be reflected in the target holding time. As a result, the target holding time can be changed to the length which is neither too long nor too short.

In the present embodiment, when the impedance value TIMPI at the time of start is in the range exceeding the value corresponding to 300° C. of the air-fuel ratio sensor 48, TIACT is set at zero as shown in FIG. 11. This is because according to the knowledge of the inventor of the present application, when the air-fuel ratio sensor 48 is in the temperature zone of 300° C. or higher, the adsorption amount is very small, and therefore, it is determined that the effect of the output shift due to the adsorbed species can be ignored. In this case, at the time point when the temperature of the sensor element section 50 reaches the activation temperature (for example, 750° C.), the sensor activation flag in step S110 is turned on. However, the present invention is not limited to this, and a very short time to a certain extent may be ensured as the target holding time.

Besides the fourth embodiment and the fifth embodiment, the target holding time may be changed based on the elapsed time (more specifically, the engine stop time period) until the start time of this time from the time of stop of the previous time, for example. It can be estimated that as the engine stop time period is longer, the adsorption amount is larger. Therefore, as the engine stop time period is longer, the target holding time may be set to be long.

In the fifth embodiment, the temperature T1 is set to be the activation temperature, but as in the first embodiment, the time T1 may be properly set to a temperature of 500° C. or the like. In such a case, if the map is created, which reflects the point that the length of the output shift time period changes in accordance with the cooling situation of the air-fuel ratio sensor 48 in the target holding time, the similar effect to that of the fifth embodiment can be obtained.

Sixth Embodiment

Basic Concept of the Sixth Embodiment

Hereinafter, the sixth embodiment will be described on the precondition that the sixth embodiment has the same system configuration as the first embodiment, and can execute the similar operation. However, in the fifth embodiment, the temperature T1 is also set to the activation temperature of the air-fuel ratio sensor 48 (in other words, the target temperature Ttgt of the heater 57) as in the fourth embodiment.

The sixth embodiment is common to the fourth and the fifth embodiments in the point that the target holding time Te in the first embodiment is changed. However, the sixth embodiment differs from the fourth and the fifth embodiments in the point of paying attention to the peak value of the rich side (hereinafter, also referred to as "rich side peak") of the air-fuel ratio sensor 48 at the time of start of the internal combustion engine 1 when the target holding time is changed.

According to the knowledge of the inventor of the present application, the following two tendencies are preferably considered in considering the effect of adsorbed species.

(1) As the amount of the adsorbed species which are adsorbed onto the sensor element section (the sensor element section 50 in the first embodiment) at the time of cooling the air-fuel ratio sensor is larger, it becomes more difficult to cause oxidation of the adsorbed species.

(2) As the atmosphere around the sensor at the time of warming-up of the air-fuel ratio sensor is richer, it becomes more difficult to cause oxidation of the adsorbed species.

As a result that oxidation of the adsorbed species is difficult to cause (inhibited), the output shift to the rich side in the process of warming-up of the air-fuel ratio sensor continues for a long period of time.

Thus, the inventor of the present application has reached the method for changing the target holding time based on the rich side peak at the time of warming-up of the air-fuel ratio sensor. That is, in the fifth embodiment, as the output shown by the air-fuel ratio sensor 48 is richer, the target holding time is set to be longer, before the activation determination during warming-up at the time of start.

Operation and Specific Processing of the Sixth Embodiment

Figure 12:
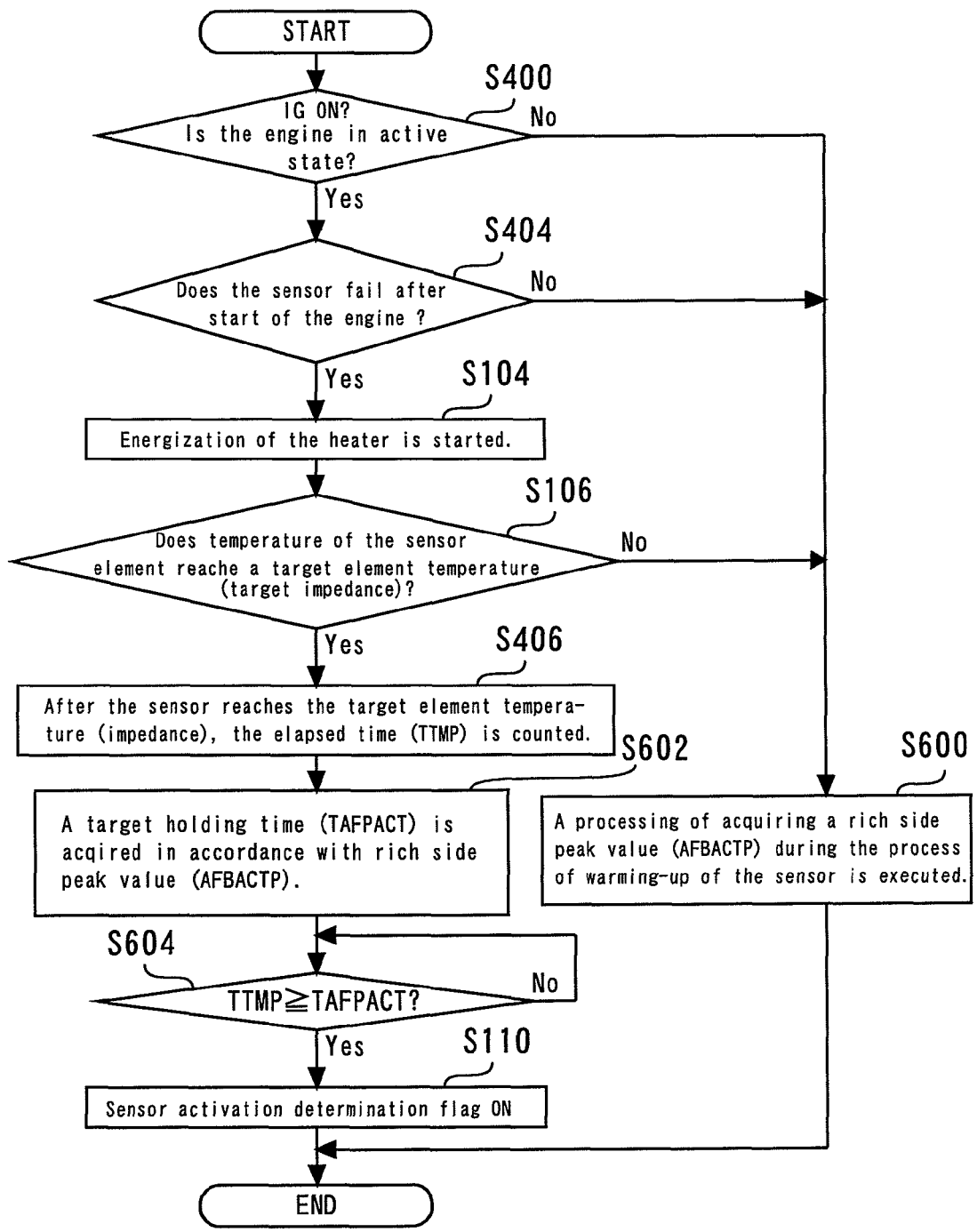
FIG. 12 is a flowchart of routines executed by the ECU 60 in a sixth embodiment.

Hereinafter, the operation of the sixth embodiment will be described with the specific processing in the sixth embodiment. FIG. 12 is a flowchart of routines executed by the ECU 60 in the sixth embodiment. In the routines of FIG. 12, the routines of the same processing contents as the routines described in the first to the fifth embodiments are assigned with the same reference signs.

FIG. 13 is a map which is stored in the ECU 60 in advance in the sixth embodiment. In the sixth embodiment, the relation of a rich side peak AFBACTP, and a target holding time (described as TAFPACT in the sixth embodiment) is empirically specified in the map as shown in FIG. 13. This map is specified so that as the rich side peak AFBACTP is richer, TAFPACT becomes longer.

In the routines of FIG. 12, steps S400 and S404 as in the fourth embodiment, and steps S104 and S106 as in the first embodiment are respectively executed first.

Here, if the temperature of the air-fuel ratio sensor 48 is still low at the time immediately after start of the internal combustion engine 1 or the like, the condition of step S106 is denied. More specifically, except for the case in which the air-fuel ratio sensor 48 is at a high temperature or the like at the time of start, the condition of step S106 is denied at least once. In such a case, the process shifts to step S600. In the routines of FIG. 12, even when the conditions are denied in steps S400 and S404, the process proceeds to step S600. In step S600, the processing of acquiring the rich side peak AFBACTP during the process of warming-up of the sensor is executed. More specifically, the output of the air-fuel ratio sensor 48 is consecutively held during execution of the present routines, and each time the process proceeds to step S600, the maximum value of the rich side output values indicated by the air-fuel ratio sensor 48 so far is set as the rich side peak AFBACTP.

In the process of repetition of execution of the routines of FIG. 12, warming-up of the air-fuel ratio sensor 48 advances. After a while, at the stage where the air-fuel ratio sensor 48 reaches the temperature T1, the condition of step S106 is confirmed. As a result, the process proceeds to step S406, and count of TTMP is started.

Subsequently, the map shown in FIG. 13 is referred to, and the target holding time TAFPACT is acquired in accordance with the value of AFBACTP which is acquired in step S600 (step S602).

Next, it is determined whether or not TTMP becomes TAFPACT or more (step S604). In this step, the process enters the loop processing until the elapsed time from the time when the air-fuel ratio sensor 48 reaches the temperature T1 exceeds the target holding time. In the sixth embodiment, the output of the air-fuel ratio sensor 48 is masked to be stoichiometry during this time period. Thereafter, at the point of time when TTMP becomes TAFPACT or more, the process exits from the loop processing. Finally, the sensor activation flag is turned on in step S104, and the routines of this time end.

According to the above processing, the point that the length of the time period of the rich side output shift changes in accordance with the rich side peak can be reflected in the target holding time. As a result, the target holding time can be changed to a more appropriate length.

In the sixth embodiment, when the value of the rich side peak is stoichiometric or lean, the rich side output shift time period can be regarded as absent. Thus, in the map of FIG. 13, TAFPACT is set as zero when AFBACTP is stoichiometry. Though not illustrated in FIG. 13, TAFPACT is also set as zero when AFBACTP is lean. Thereby, when a rich side output shift is absent, the activation flag can be quickly turned on after the air-fuel ratio sensor 48 reaches the activation temperature. As a result, when the effect of the adsorbed species can be ignored, the activation determination of the air-fuel ratio sensor 48 can be quickly performed correspondingly, and the air-fuel ratio feedback control can be resultantly started early.

In the sixth embodiment, the temperature T1 is set at the activation temperature, but as in the first embodiment, the temperature T1 may be properly set at a temperature of 500° C. or the like. In such a case, the target holding time is changed to be longer as the value of the rich side peak is richer, and thereby, the similar effect to the sixth embodiment can be obtained.

Seventh Embodiment

In the first to the sixth embodiments, the condition (ii) described in the first embodiment is determined, that is, it is determined whether the effect of the adsorbed species is sufficiently removed from the output of the air-fuel ratio sensor 48, by measuring the time while the air-fuel ratio sensor 48 is warmed up by the heater 57. Meanwhile, for example, an integrated air amount, an element temperature or an element admittance is measured without being limited to the method of time measurement, and by this measurement result, it may be determined that the effect of the adsorbed species is sufficiently removed from the output of the air-fuel ratio sensor 48.

Eighth Embodiment

The present invention is not limited to the mode of determining the activation state of the air-fuel ratio sensor 48 by the presence or absence of the lapse of a predetermined time from the time of the desorption start temperature as in each of the aforementioned embodiments. The predetermined time is set to pass the point of time when the exhaust gas sensor reaches the activation temperature by heating by the heater, and has such a length that the output shift of the exhaust gas sensor due to the adsorbed species is substantially eliminated. According to the present invention, as another example, the activation state of the air-fuel ratio sensor 48 may be determined based on whether or not the output shift of the air-fuel ratio sensor 48 due to the adsorbed species is eliminated finally. More specifically, the time from the start to the time point when the adsorbed species are almost eliminated is measured, and by the fact that the time passes this time point, the activation state of the exhaust gas sensor may be determined.

The invention claimed is:

1. A device for determining activation of an exhaust gas sensor, comprising:
a heater for heating the exhaust gas sensor at a time of start of an internal combustion engine;
acquiring means which acquires a physical amount having a correlation with a temperature of the exhaust gas sensor; and
determining means which determines an activation state of the exhaust gas sensor based on whether or not such a time period that desorbed species are substantially eliminated from the exhaust gas sensor has elapsed after the adsorbed species which are exhaust gas components adsorbed on the exhaust gas sensor start to be desorbed, at the time of start of the internal combustion engine, wherein
the determining means includes
temperature determining means which determines whether or not the temperature of the exhaust gas sensor has reached a predetermined temperature which is set in advance within a temperature region not lower than a desorption start temperature which is a temperature at which the adsorbed species which are the exhaust gas components adsorbed on the exhaust gas sensor start to be desorbed, based on the physical amount, and
activation determining means which determines the activation state of the exhaust gas sensor based on an elapsed time from a time point when the temperature of the exhaust gas sensor reaches the predetermined temperature.

2. The device for determining activation of an exhaust gas sensor according to claim 1,
wherein the activation determining means determines the activation state of the exhaust gas sensor based on the temperature of the exhaust gas sensor and the elapsed time, and
the activation determining means includes
activation temperature determining means which determines the activation state of the exhaust gas sensor based on whether or not the exhaust gas sensor reaches an activation temperature, and
activation determination prohibiting means which prohibits the exhaust gas sensor from being determined as reaching the activation state irrespective of a determination result of the activation temperature determining means until the elapsed time exceeds a predetermined time.

3. The device for determining activation of an exhaust gas sensor according to claim 2, further comprising:
means which sets the predetermined time so that a time at which prohibition by the activation determination prohibiting means is released is past a time at which the exhaust gas sensor reaches the activation temperature by the heater which heats the exhaust gas sensor at the time of start of the internal combustion engine.

4. The device for determining activation of an exhaust gas sensor according to claim 1,
wherein the predetermined temperature is an activation temperature of the exhaust gas sensor, and
the activation determining means determines that the exhaust gas sensor is in the activation state when a predetermined time elapses after the exhaust gas sensor reaches the activation temperature.

5. The device for determining activation of an exhaust gas sensor according to claim 1,
wherein the activation determining means determines the activation state of the exhaust gas sensor based on whether or not the elapsed time has exceeded a predetermined time, and
the predetermined time is set so as to pass a time point at which the exhaust gas sensor reaches an activation temperature by heating of the heater, and is set at such a length that an output shift of the exhaust gas sensor due to adsorbed species is substantially eliminated.

6. The device for determining activation of an exhaust gas sensor according to claim 1,
wherein the predetermined temperature is a temperature selected from a temperature region from 300° C. to 700° C. inclusive.

7. The device for determining activation of an exhaust gas sensor according to claim 1,
wherein the physical amount acquired by the acquiring means is an impedance or an admittance of the exhaust gas sensor, and
the predetermined temperature is a temperature selected from a temperature region not less than 400° C.

8. The device for determining activation of an exhaust gas sensor according to claim 2, further comprising:

property acquiring means which acquires a fuel property of an internal combustion engine; and property condition time setting means which sets the predetermined time to a different length in accordance with a fuel property acquired by the property acquiring means.

9. The device for determining activation of an exhaust gas sensor according to claim 2, further comprising:

rich peak acquiring means which acquires a peak value at a rich side of an air-fuel ratio indicated by an output of the exhaust gas sensor in a time period in which the exhaust gas sensor is inactive, during start of an internal combustion engine, and rich condition time setting means which sets the predetermined time to be longer as the air-fuel ratio acquired by the rich peak acquiring means is larger to a rich side.

10. The device for determining activation of an exhaust gas sensor according to claim 2, further comprising:

adsorption amount acquiring means which acquires an amount having a correlation with an adsorption amount at a time of stop, which is an amount of gas components adsorbed onto the exhaust gas sensor while an internal combustion engine is stopped; and adsorption amount condition time setting means which changes the predetermined time in accordance with an amount which is acquired by the adsorption amount acquiring means.

11. The device for determining activation of an exhaust gas sensor according to claim 10, wherein the adsorption amount acquiring means includes means for acquiring at least one of a water temperature, an intake air temperature and an oil temperature at the time of start of the internal combustion engine, an exhaust gas sensor temperature at the time of start of the internal combustion engine and a physical amount having a correlation with the exhaust gas sensor temperature, and a stop time period which is a length of a time period from stop of the internal combustion engine to a beginning of start of the internal combustion engine, and the adsorption amount condition time setting means includes means which sets the predetermined time to be longer as the water temperature or the oil temperature at the time of start of the internal combustion is lower, as the exhaust gas sensor temperature at the time of start of the internal combustion engine is lower, or the stop time period is longer.

12. The device for determining activation of an exhaust gas sensor according to claim 2, further comprising:

rich peak acquiring means which acquires a peak value at a rich side of an air-fuel ratio indicated by an output of the exhaust gas sensor in a time period in which the exhaust gas sensor is inactive, during start of an internal combustion engine, and rich condition time setting means which sets the predetermined time to be longer as the air-fuel ratio acquired by the rich peak acquiring means is larger to a rich side, and instant activation determining means which determines that the exhaust gas sensor is in the activation state when the exhaust gas sensor reaches the activation temperature, when an air-fuel ratio acquired by the rich peak acquiring means indicates stoichiometry or a value at a lean side.

13. The device for determining activation of an exhaust gas sensor according to claim 1, wherein the determining means determines whether after adsorbed species which are exhaust gas components adsorbed onto the exhaust gas sensor start to be desorbed, such a time period that the adsorbed species are substantially eliminated from the exhaust gas sensor has elapsed or not, based on a result of measurement with at least one of an integrated air amount of the internal combustion engine, an element temperature of the exhaust gas sensor, and an element admittance of the exhaust gas sensor, as a target.

14. A control device for an internal combustion engine, comprising:

an exhaust gas sensor;

the device for determining activation of the exhaust gas sensor according to claim 1 which performs determination of activation of the exhaust gas sensor;

feedback control means for performing feedback control of an air-fuel ratio of the internal combustion engine based on an output of the exhaust gas sensor; and feedback control starting means which starts control by the feedback control means based on a result of the determination of the device for determining activation, at a time of start of the internal combustion engine.

15. The control device for an internal combustion engine according to claim 14, wherein the exhaust gas sensor is a critical current type air-fuel ratio sensor.

16. The device for determining activation of an exhaust gas sensor according to claim 2, further comprising:

adsorption amount acquiring means which acquires an amount having a correlation with an adsorption amount at a time of stop, which is an amount of gas components adsorbed onto the exhaust gas sensor while an internal combustion engine is stopped;

adsorption amount condition time setting means which changes the predetermined time in accordance with an amount which is acquired by the adsorption amount acquiring means; and instant activation determining means which determines that the exhaust gas sensor is in the activation state when the exhaust gas sensor reaches the activation temperature, when an adsorption amount indicated by the adsorption amount acquiring means is below a predetermined reference value.

17. A device for determining activation of an exhaust gas sensor, comprising:

a heater for heating the exhaust gas sensor at a time of start of an internal combustion engine;

acquiring means which acquires a physical amount having a correlation with a temperature of the exhaust gas sensor; and determining means which determines an activation state of the exhaust gas sensor based on whether or not such a time period that desorbed species are substantially eliminated from the exhaust gas sensor has elapsed after the adsorbed species which are exhaust gas components adsorbed on the exhaust gas sensor start to be desorbed, at the time of start of the internal combustion engine, wherein the heater heats the exhaust gas sensor to a target temperature at the time of start of the internal combustion engine, and the determining means includes activation determining means which determines the activation state of the exhaust gas sensor based on an elapsed time from a time point when the temperature of the exhaust gas sensor reaches a predetermined temperature which is set in advance in a temperature region not higher than the target temperature, after start of heating of the heater.

* * * * *